(12) United States Patent
Benner et al.

(10) Patent No.: US 11,039,746 B1
(45) Date of Patent: Jun. 22, 2021

(54) NON-SLIDING AND NON-SUTURED CONTACT LENS SYSTEM FOR OPHTHALMIC PROCEDURES

(71) Applicant: DRUG DELIVERY COMPANY, LLC, Salisbury, MD (US)

(72) Inventors: Jeffrey D. Benner, Salisbury, MD (US); Steven M. Cohen, Saint Petersburg, FL (US); Christopher Forrest Lumpkin, Evergreen, CO (US)

(73) Assignee: Drug Delivery Company, LLC, Salisbury, MD (US)

( * ) Notice: Subject to any disclaimer, the term of this patent is extended or adjusted under 35 U.S.C. 154(b) by 190 days.

(21) Appl. No.: 16/278,971

(22) Filed: Feb. 19, 2019

Related U.S. Application Data

(63) Continuation-in-part of application No. 15/902,578, filed on Feb. 22, 2018, now Pat. No. 10,258,233.
(Continued)

(51) Int. Cl.
*A61B 3/00* (2006.01)
*A61B 3/125* (2006.01)
(Continued)

(52) U.S. Cl.
CPC .............. *A61B 3/125* (2013.01); *A61B 3/117* (2013.01); *A61B 17/0231* (2013.01); *A61F 9/00* (2013.01);
(Continued)

(58) Field of Classification Search
CPC .. A61B 3/14; A61B 3/13; A61B 3/102; A61B 3/103; A61B 3/107; A61B 3/117;
(Continued)

(56) References Cited

U.S. PATENT DOCUMENTS 5,070,290 A 12/1991 Iwasa et al.
5,479,222 A 12/1995 Volk
(Continued)

OTHER PUBLICATIONS

Overview of "Ocular Vitrectomy Lens Rings" from Ocular Instruments, Inc. (2001).
(Continued)

*Primary Examiner* — Mustak Choudhury
(74) *Attorney, Agent, or Firm* — Rosenberg, Klein & Lee

(57) ABSTRACT

A contact lens assembly for non-sliding, non-sutured, hands-free ophthalmic procedures utilizes a magnetically actuated anchoring mechanism operatively coupled between the contact lens assembly and a modified eye speculum applied to eyelids during ophthalmic procedure. The anchoring mechanism is configured with magnetically cooperating anchoring members, one coupled to the contact lens assembly, and another secured to a wire loop member of the modified eye speculum. After the eye speculum is applied to the eyelids to displace and stabilize the eyelids and secure the anchoring member in place, and the contact lens assembly is placed on the cornea of the eye and centered, he magnetically cooperating anchoring members are brought in contact, and thus secure the contact lens assembly at the surgical site.

16 Claims, 15 Drawing Sheets

Related U.S. Application Data which is a continuation of application No. 15/497,827, filed on Apr. 26, 2017, now Pat. No. 9,936,871.

(60) Provisional application No. 62/329,292, filed on Apr. 29, 2016.

(51) Int. Cl.
| | | |
|---|---|---|
| *A61F 9/00* | (2006.01) | |
| *A61B 17/02* | (2006.01) | |
| *A61B 3/117* | (2006.01) | |
| *G02C 7/04* | (2006.01) | |
| *A61B 17/00* | (2006.01) | |

(52) U.S. Cl.
CPC ...... *G02C 7/04* (2013.01); *A61B 2017/00946* (2013.01); *A61F 2009/0052* (2013.01)

(58) Field of Classification Search
CPC ....... A61B 3/125; A61B 3/152; A61B 3/1173; A61B 17/0231; A61B 2017/00946; A61F 9/00; A61F 9/009; A61F 9/008; A61F 9/00825; A61F 9/00834; A61F 9/00745; A61F 9/00821; A61F 2009/0052; A61F 2009/0087; G02C 7/04
See application file for complete search history.

(56) References Cited

U.S. PATENT DOCUMENTS

| | | | |
|---|---|---|---|
| 5,963,301 A | 10/1999 | Volk | |
| 6,120,147 A | 9/2000 | Vikfvinkel et al. | |
| 8,070,290 B2 | 12/2011 | Gille et al. | |
| 8,861,061 B1* | 10/2014 | Graham | A61B 3/117 359/219.1 |
| 9,339,184 B2 | 5/2016 | Hassan et al. | |
| 2002/0103421 A1* | 8/2002 | Putrino | A61B 17/0231 600/236 |
| 2002/0103481 A1* | 8/2002 | Webb | A61F 9/009 606/5 |
| 2009/0182312 A1* | 7/2009 | Gertner | A61F 9/008 606/4 |
| 2010/0036488 A1 | 2/2010 | de Juan, Jr. et al. | |
| 2012/0099077 A1* | 4/2012 | Abt | A61B 3/125 351/219 |
| 2012/0283557 A1 | 11/2012 | Berlin | |
| 2013/0165911 A1* | 6/2013 | Raksi | A61F 9/009 606/5 |
| 2015/0153588 A1 | 6/2015 | Angelini et al. | |
| 2015/0327764 A1 | 11/2015 | Graham et al. | |
| 2017/0079528 A1* | 3/2017 | Farley | A61B 3/13 |

OTHER PUBLICATIONS

International Search Report from related PCT Application No. PCT/US2017/029606 (dated Sep. 15, 2017).

\* cited by examiner

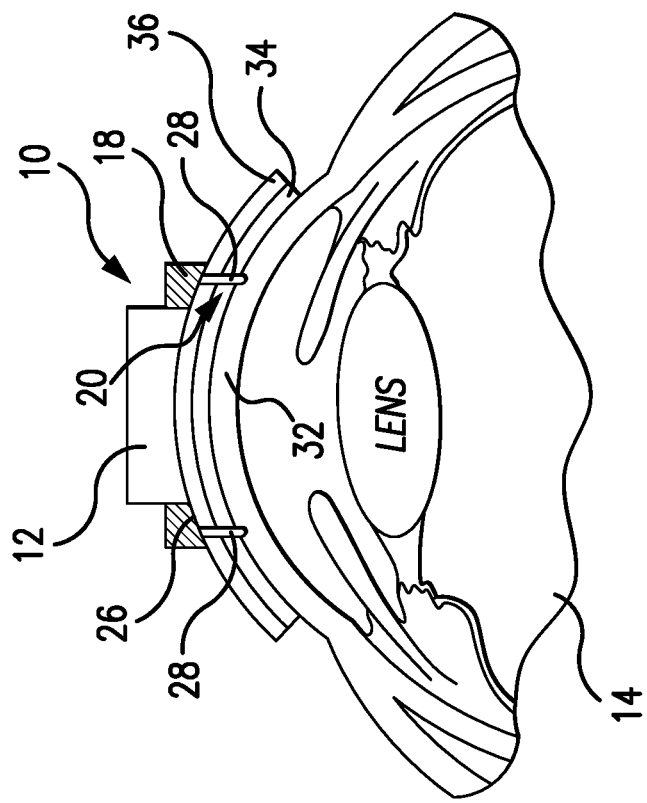
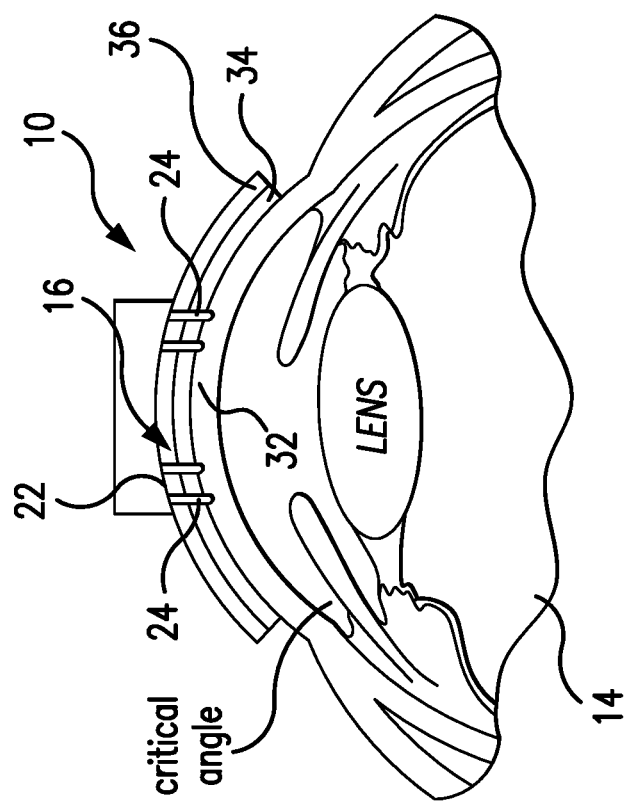

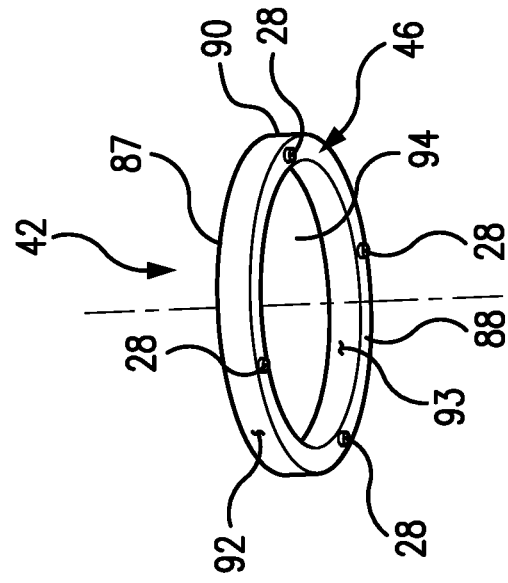
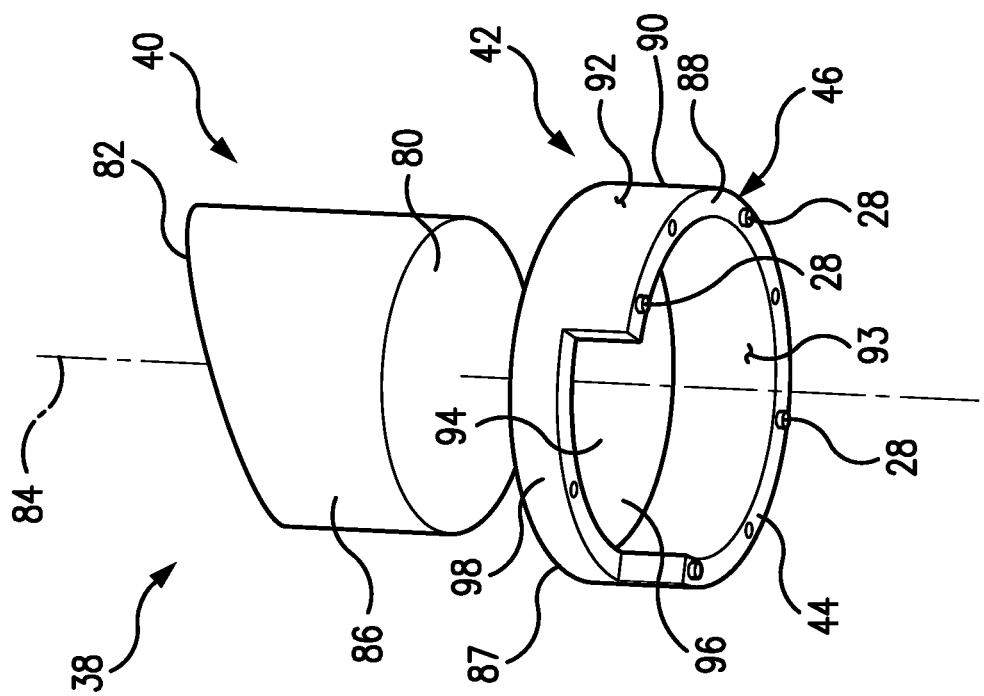

NON-SLIDING AND NON-SUTURED CONTACT LENS SYSTEM FOR OPHTHALMIC PROCEDURES

RELATED APPLICATIONS

This Application is a Continuation-in-Part Application of patent application Ser. No. 15/902,578 filed on 22 Feb. 2018, currently pending, which is a Continuation of patent application Ser. No. 15/497,827 filed on 26 Apr. 2017, issued as U.S. Pat. No. 9,936,871, which was based upon Provisional Patent Application Ser. No. 62/329,292 filed on 29 Apr. 2016.

FIELD OF THE INVENTION

The present invention is directed to the field of ophthalmic surgical intervention, and particular to contact lens used in ophthalmic surgeries.

More in particular, the present invention is directed to corneal (and macular) contact lenses, as well as gonioprisms, used in vitreoretinal surgeries (procedures), which allow a surgeon to visualize the macula and other structures of the eye under surgery at high magnification.

In addition, the present invention is directed to contact lenses used in ophthalmic procedures which are configured with an anchoring mechanism which stabilizes and centers the lens on the cornea of the eye (or other desired site of procedure) in a "hands-free" manner without the need for monitoring and manual positioning of the contact lens during ophthalmic procedures.

Further, the subject system is directed to a contact lens anchoring system which does not require suturing for stabilization and centration during the ophthalmic procedure, and thus is free of superficial bleeding from the conjunctiva caused by the suturing.

The present invention is further directed to a non-sutured and hands-free contact lens anchoring system for ophthalmic surgeries which effectively stabilizes and centers the contact lens on the cornea of the eye during surgery and which is prevented from sliding on the area of interest by a magnetic connection mechanism configured for quick attachment of the contact lens to an eyelid speculum used in the ophthalmic procedure, thus temporarily anchoring the contact lens to the cornea. The subject magnetic mechanism is easily deactuated to remove the lens from the eye when the ophthalmic procedure is completed.

Additionally, the present system is directed to a suture free, non-sliding stabilization anchoring system for a corneal (or macular) contact lens, as well as gonioprism contact lens, used in vitreoretinal surgeries, which is configured with a pair of magnetically cooperating members, where one magnetically cooperating member is secured to the eyelid speculum, and another magnetically cooperating member is attached to a contact lens holder (of the contact lens itself) via a wire member, which is secured to the contact lens or the contact lens holder, and where during the procedure the first and second magnetically cooperating members are brought in contact to magnetically engage one with another, thus anchoring the contact lens or the contact lens holder to the cornea without any trauma to the eye tissues.

In overall concept, the present invention is directed to a contact lens assembly for ophthalmic procedures performed with the use of an eyelid speculum for displacing the eyelids of a patient, where the contact lens assembly includes a contact lens adapted for contacting an eye of the patient, a contact lens holder secured to the contact lens, and an anchoring magnetically actuated mechanism releasably secured between the contact lens holder and the eyelid speculum for anchoring and stabilizing the contact lens (and/or the contact lens holder) at a predetermined positional location during the ophthalmic procedure, where the anchoring mechanism includes a wire member coupled to the contact lens holder and a pair of magnetically cooperating units, one of which is positioned on the wire member to being displaced therealong, and another of which is secured to the eyelid speculum. When the eyelid speculum is applied to the eyelids, and the contact lens (with the contact lens holder) is positioned on the eye under surgery, the magnetically cooperating units are brought in contact one with another for magnetically supported interconnection therebetween resulting in anchoring and stabilization of the contact lens (and/or the contact lens holder) in the predetermined position on the eye undergoing the ophthalmic procedure.

BACKGROUND OF THE INVENTION

Corneal contact lenses are a critical part of vitreoretinal surgery, especially macular surgery. The contact lenses allow a surgeon to visualize the macular as well as other structures of the eye at high magnification. Surgeons typically employ a separate lens that can be placed directly on the eyeball and allow focusing to be extended to the retina and other areas in the back of the eyeball.

In order to be effective, a contact lens must be stably positioned and centered on the cornea of the eye at the site of the surgery. This is difficult to achieve due to the cornea curved contouring. The slipperiness is made worse by the use of viscous coupling agents (such as, for example, viscoelastics or hydroxymethyl cellulose), which are used to avoid bubble formation beneath the contact lens during the surgery.

The lens placed on the eyeball floats on a thin layer of fluid and tends to slide about the surface of the eye. In order to overcome the sliding displacement and to hold the lens in place, a surgeon or a surgeon's assistant constantly monitors the lens position and uses a rod or other extension (handle) to push the lens back to a desired location. In order to perform this task, the surgeon or surgeon's assistant must have a profound experience in vitreoretinal surgery which is not always the case.

For example, U.S. Pat. No. 5,070,290, describes the gonioscopy, which is a technique used for viewing inner portions (such as the retina and the anterior chamber angle) of the eye for evaluation, management, and classification of normal and abnormal structures of the eye. The gonioscopy technique uses devices known as gonioscopes to enhance visibility of the trabecular meshwork and anterior chamber angle during surgical procedures. The gonioscope is hand-held by a surgeon in place over the patient's cornea while he/she performs the surgical procedure.

The gonioscope described in U.S. Pat. No. 8,070,290 includes the Hill gonioprism positioned on a patient's eye. The gonioscopic optical element, which includes one or several lens, such as optical prism(s), is received in a lens retainer, and a handle or a grip is attached to the lens retainer. During the surgical procedure, the gonioscopic optical element is positioned over or on the patient's eye, e.g. the cornea of the eye.

A light source is used during the surgery which emits light toward the patient's eye. The light source may be configured such that light from the source illuminates the patient's eye, the anterior chamber, and the eye structures near the anterior chamber, e.g. trabecular meshwork, such that one or more of these structures reflect(s) light incident from the light source.

The light source and the prism(s) is (are) arranged in such a fashion that the light from the light source is reflected by the patient's eye (or specific optical structures), traverses the gonioscopic prism(s), and is redirected, e.g., refracted and diffracted, by the gonioscopic prisms. An image is formed of at least part of the patient's eye and this image is viewed using a microscope.

The handle of the gonioscope described in '290 patent is used to stabilize and centralize the entire gonioscope structure. This arrangement generally requires assistance of a surgeon assistant to manipulate the handle of the gonioscope during the procedure.

Landers has improved upon the gonioscope prism requiring manual manipulation of the handle during the ophthalmic procedure surgery, and provided a "hand-free" solution for the problem which eliminates the need for a surgeon assistant to manually stabilize and centralize the contact lens.

The Landers' system uses a lens ring which circumferentially envelopes sides of the contact lens, and serves as the lens holder. To stabilize and centralize the contact lens at the desired site during the procedure, the lens ring is secured to the conjunctiva/sclera with a pair of fixation sutures. The contact lens is placed inside the lens ring which remains in place by the fixation sutures, and thus, the contact lens is maintained in place and sutured throughout the duration of the macular surgery.

Fixation sutures, however, are not welcomed by a majority of ophthalmologists, especially glaucoma surgeons, due to traumatic effects of the fixation sutures to the cornea or sclera of the eye. In addition to the traumatic nature of the fixation sutures (which typically cause bleeding which can obscure view of the surgical site), if the sutures are excessively tight, the cornea can be disturbed and the sutures may break during the surgery, which is definitely a disadvantage of the suturing approach. On the other hand, if the sutures are too loose, the displacement of lens may occur, which can undermine the surgery efficiency.

Since the Landers development, various solutions for "suture-less" contact lens stabilization have been developed. For example, as presented in U.S. Pat. No. 5,963,301, the lens is constructed with a flange that is shaped to conform to the general curvature of an average eye. In order to be attached to the eye surface, and thus stabilizing the lens in place, the flange is formed with a number of peripheral openings or recesses sized to accommodate various types of instruments to be inserted into the eye during the surgery. The flange is formed with fittings to which a vacuum is applied in order to pull the flange into contact with the sclera of the eye by creating a vacuum between the flange and eye to enhance holding the lens device in position.

Another method for overcoming the problem of contact lens movement during surgery is disclosed in U.S. Pat. No. 6,120,147 where the lens are replaced with flexible lens having a relatively flexible flange which is fixed in place by capillary action.

U.S. Patent Application Publication No. 2014/0307229 and related U.S. Pat. No. 9,339,184 describe a contact lens for vitreoretinal surgery where a contact lens assembly has a central lens and a circumscribing flange. The lens has an eye contact surface shaped generally to a radius of curvature of a cornea of an eye. The flange comprises a sterile sponge-like liquid absorbent flexible material having a central aperture for fitting snuggly about an outer circumference of the lens and extending radially outward therefrom.

During the procedure, the lens is mated with a flange and the lens/flange assembly is then placed on the wetted eye of a patient. Additional wetting compound, such as sterile saline solution, is then spread onto the flange until the flange is generally situated. The lens can then be moved as necessary for viewing and the wetted flange holds the lens in a desired position.

It has been found that most of the prior art devices slide off of the cornea during the surgery. The surgeon, or the surgeon's assistant, must push the lens back to the center of the cornea a number of times during critical steps of the surgery. This may cause loss of the surgical field at a crucial moment. Thus, the suture-less systems currently available, are not preferred by many surgeons. The surgeons use the sutured lens ring even though it takes additional time and causes superficial bleeding from the conjunctiva.

It is highly desirable to provide a suture-free and hands-free non-sliding corneal contact lens anchoring and stabilization system for vitreoretinal surgery which does not require monitoring and manual positioning of the lens during the surgery and which provides hands-free effective stabilization and centralization of the lens during a surgical procedure in trauma-free manner.

One of the important topics discussed among glaucoma surgical specialists is micro invasive glaucoma surgery, further referred to herein as MIGS. The MIGS refers to a group of relatively recent glaucoma surgery techniques that are gentler and involve less tissue disruption than traditional glaucoma surgeries (such as trabeculectomy and shunts).

The glaucoma specialists indicate that there is a significant learning curve in order to master MIGS technique. Operating directly on the tiny trabecular meshwork is challenging. Obtaining visualization of the angle is the most difficult part of the learning curve and the key to mastering this surgery. The critical angle of the peripheral cornea may cause total internal reflectivity of light. For that reason, special contact lenses are needed to allow visualization of the angle structures.

Even with a surgical gonioprism, the critical angle surgery is difficult to perform. Mastering the usage of the current surgical gonioprism is a significant barrier for many surgeons. In order to visualize the angle structures, a surgeon rotates the patient's head to the side by 30°, to the microscope 30°, and to steady a hand-held surgical gonioprism on the cornea with their non-dominant hand (as shown, for example, in U.S. Pat. No. 8,070,290). This requires a significant amount of practice and steady hands. The surgeon cannot learn the technical steps of the MIG surgery, such as implanting the stent or cutting into the trabecular meshwork, until they can consistently obtain a steady view of the angle.

Glaucoma surgeons are universally opposed to placing fixation sutures. They do not want to cause any trauma to the cornea or sclera of the eye. Simplifying and improving the visualization of the critical angle during the surgery, without causing tissue injury by fixating sutures can remove the barriers that are currently limiting adoption of this newest type of glaucoma surgery, i.e., MIGS.

U.S. Patent Application Publication No. 2012/0099077 to Abt describes an ophthalmic optics (lens) which includes an aspheric anterior surface and a posterior surface having a shape substantially corresponding to the shape of a human cornea. In order to support the lens on the cornea, Abt uses a surrounding flange. Adhesive, weights or fibers (for the lens stabilization) are embedded in the tabs of the flange for registering with the sclera to create stabilization forces by the tabs' interaction with the sclera.

In Abt, the stabilizing structures (which are embedded in the tabs of the flange) do not come in contact with the tissues of the eye at the operation site. They are positioned above the eye tissues at the sclera (and thus are laterally displaced from the operation site) and "float" above the sclera area separated from the sclera tissues through the layer of the tear film and viscous layer. This "floating" on the slippery film does not provide a reliable stabilization of the lens at the operation site in Abt arrangement.

Abt's stabilizing mechanism produces shear forces displaced laterally from the cornea area and applied to the sclera (away from the cornea), and is neither formed integrally with the bottom surface of the lens nor extends vertically downward from the bottom of the lens into contact with the procedure site (such as the cornea).

The only structure in Abt system which does penetrate through the tear film of the eye are trocar cannulas. However, Abt does not consider the trocar cannulas as a mechanism for securing the optical lens to the eye of the patient. Abt emphasizes that the fastening means include packing material and/or mechanical fasteners, which are used to secure the optical lens to the patient's eye to stabilize the optical element on the eye and permit the appropriate insertion of the trocar cannulas. Thus, in Abt, trocar cannulas by themselves do not constitute the anchoring mechanism, and other fastening elements are used which facilitate the insertion of the trocar cannulas.

In Abt, the trocar cannulas are dimensioned in the mm range, and penetrate deep into sclera area. It is understood that such trocar cannulas dimensions are dictated by the operational requirements, however, they create a highly traumatic action on the tissues of the eye.

Another disadvantage of Abt is that the lens "is self-retaining on the eye through capillary attraction". The stability of the lens in Abt relies on a capillary attraction, which is not desirable since the capillary attraction forces tend to pull blood and air bubbles beneath the contact lens during surgery. This phenomenon can impair the surgeon's visualization during critical moments of surgical procedure.

It would be highly desirable to provide a reliable mechanism which can anchor and stabilize the contact lens in a non-sliding alignment with the surgical area of the eye in a suture-free, non-invasive and trauma-free fashion, without the need for manual repositioning and centralization of the contact lens (and/or contact lens holder) during the operation.

SUMMARY OF THE INVENTION

It is therefore an object of the present invention to provide a contact lens assembly for ophthalmic procedures which is capable of attaining a non-sliding non-sutured hand-free operation for the lens stabilization and centralization during a vitreoretinal surgery.

It is another object of the present invention to provide a contact lens assembly equipped with a reliable anchoring system capable of hands-free stabilization and centralization of the contact lens assembly at a desired site of procedure in a non-sutured trauma-free manner.

In one aspect, the present invention is directed to a contact lens assembly for ophthalmic procedures, which comprises an optical element (such as a contact lens), a contact lens holder, and an anchoring/stabilizing mechanism configured to anchor and stabilize the contact lens at the surgical site without the need for a surgeon to manually adjust the position of the contact lens during the procedure.

The anchoring mechanism is contemplated in various configuration, for example, realized as the magnetically actuated anchoring/stabilizing mechanism, or implemented with microstructures disposed at predetermined positions on the eye contact surface of the optical element (or the bottom surface of the contact lens holder) which creates an anchoring action for the optical element at a desired procedure site when the microstructures are brought in contact with tissues of the eye (such as the superficial layer of the eye cornea) during an ophthalmic procedure, or equipped with a mechanism for securing the contact lens (or the contact lens holder) to the eyelid speculum for stabilizing the contact lens in place during the procedure.

In one aspect, the present invention is directed to a contact lens assembly equipped with a reliable and simple in use anchoring/stabilizing mechanist for ophthalmic procedures, which comprises an optical element (such as a contact lens) and an anchoring mechanism which constitutes a magnetically actuated connection for quick attachment of the contact lens to the eyelid speculum used on the ophthalmic procedure.

The subject anchoring mechanism may be configured with a pair of magnetically cooperating anchoring members (units), with one anchoring member being secured to the contact lens holder, while another being secured to the eyelid speculum used in the operation for the eyelid's displacement and stabilization. For being magnetically cooperative, the first and second anchoring members are fabricated from magnetically attractable materials selected from a group consisting of a magnetic material, metal (or ferrous) material, and their combination, meaning that at least one of the anchoring members is made from a magnetic material, while another can be made from a magnetic material or a ferrous material. For example, when the anchoring member secured to the contact lens holder is fabricated from a magnetic alloy, the anchoring member secured to the eye speculum may be manufactured either as a magnet or as a ferrous plate. When the magnetically cooperating anchoring members are brought into contact, they become magnetically engaged one with another, and thus anchor the contact lens in a stabilized position at the surgical site of the ophthalmic procedure.

The subject contact lens assembly for ophthalmic procedures comprises a contact lens (for example, corneal lens or a gonioprism contact lens) adapted for contacting an eye of a patient, and a contact lens holder secured (releasably or permanently) to the contact lens.

The eye speculum, which contributes to the subject anchoring mechanism, is configured with pair of radially spreading speculum arm members, each ending in a wire loop member, which are applied to the eyelids of a patient during ophthalmic procedure to displace and stabilize the eyelids.

The subject magnetically actuated anchoring mechanism is configured for retaining the contact lens assembly at a selected procedure site during the ophthalmic procedure, and is operatively coupled between the eye speculum and the contact lens holder (or the contact lens).

The anchoring mechanism includes a first and a second magnetically cooperating anchoring members, wherein the first anchoring member is secured to at least one of the wire loop members of the eye speculum, wherein the second anchoring member is operatively coupled to the contact lens holder (or the contact lens), and wherein, during the ophthalmic procedure, the first and second anchoring member are disposed in a magnetic contact one with another, thus releasably anchoring and stabilizing the contact lens at a desired position relative to the eye of the patient.

The subject anchoring mechanism further includes a wire member which is secured, at one end thereof, to the contact lens holder (or directly to the contact lens). The second anchoring member is attached to the wire member in a displaceable relationship therewith along the wire member.

Preferably, a rotational mechanism is operatively coupled between the wire member and the contact lens holder to support rotational displacement of the contact lens holder relative the longitudinal axis of the wire member for adjustability of the contact lens orientation. In addition, to enhance the positional adjustability, the contact lens is co-axially displaceable about the longitudinal axis of the contact lens holder.

The contact lens holder may be formed of a substantially cylindrical tubing for receiving the contact lens. The contact lens holder may be fixedly secured (releasably or permanently) to the contact lens at a periphery of the contact lens, and may be adhered to the contact lens at at least a portion of the contact lens periphery.

When, during the ophthalmic procedure, the pair of loop members of the eyelid speculum are radially displaced each from the other for maintaining the patient's eyelid in a stable displaced position, the first anchoring member is stably positioned at a predetermined placement at the eyelids.

In another aspect, the present invention is directed to a method for performing an ophthalmic procedure using a non-sliding non-sutured, hands-free contact lens assembly held in place with a reliable magnetically actuated anchoring/stabilizing mechanism.

The subject method includes the steps of:

configuring a contact lens assembly with a contact lens adapted for contacting an eye of a patient, and a contact lens holder secured to the contact lens;

configuring an eye speculum with a pair of speculum arm members, each terminating in a wire loop member, and a first magnetically cooperative anchoring member affixed at a predetermined position on a respective wire loop member; and configuring a magnetically actuated anchoring mechanism between the contact lens assembly and the respective wire loop member of the eye speculum, wherein the anchoring mechanism includes the first magnetically cooperative anchoring member (on the eye speculum) and a second magnetically cooperative anchoring member secured to the contact lens assembly.

During the ophthalmic procedure, the subject method is supported by the following step:

placing said contact lens assembly over a desired procedure site;

applying the eye speculum to the eyelids to displace and stabilize the eyelids, thus securing the first magnetically cooperative anchoring member at a predetermined position;

bringing the first and second magnetically cooperative anchoring members in contact one with another;

performing the ophthalmic procedure; and upon completion of the ophthalmic procedure, disengaging the first and second magnetically cooperative anchoring members, thus de-actuating the anchoring mechanism;

removing the contact lens assembly from the operational side; and removing the eye speculum from the patient's eye.

These and other objects of the present invention will become apparent after reading further description of the preferred embodiment(s) of the subject invention in conjunction with the accompanying Patent Drawings.

BRIEF DESCRIPTION OF THE DRAWINGS

FIGS. 1A-1B are schematic representations of the subject contact lens (FIG. 1A) and contact lens holder/assembly (FIG. 1B) attached to the cornea of the eye during the surgical procedure;

FIG. 3A is a view of the subject lens from the bottom, and FIG. 4A is a side view of the subject contact lens, showing microstructures placed on the bottom of the contact lens;

FIG. 3B is a bottom view of the lens holder assembly, and FIG. 4B is a side view of the subject lens/holder assembly;

FIGS. 6A-6B show an exploded view of the gonioprism contact lens assembly, where FIG. 6A is a side view and FIG. 6B is a bottom view of the subject gonioprism contact lens assembly;

FIGS. 7A-7B show a side view (FIG. 7A) and a bottom view (FIG. 7B) of the subject gonioprism lens holder in an alternative embodiment;

FIG. 15A depicts the modified eye speculum applied to the eye of a patient during an ophthalmic procedure to displace and stabilize the eyelids, FIG. 15B depicts schematically the anchoring/stabilization of the subject contact lens assembly at the operational site through the magnetic connection between the speculum based anchoring member and the lens holder based anchoring member, and FIG. 15C is a schematic representation of the subject gonioprism contact lens assembly secured to the eye during a surgical procedure by the use of the subject magnetically actuated anchoring mechanism.

DETAILED DESCRIPTION OF THE PREFERRED EMBODIMENTS

Figure 2:
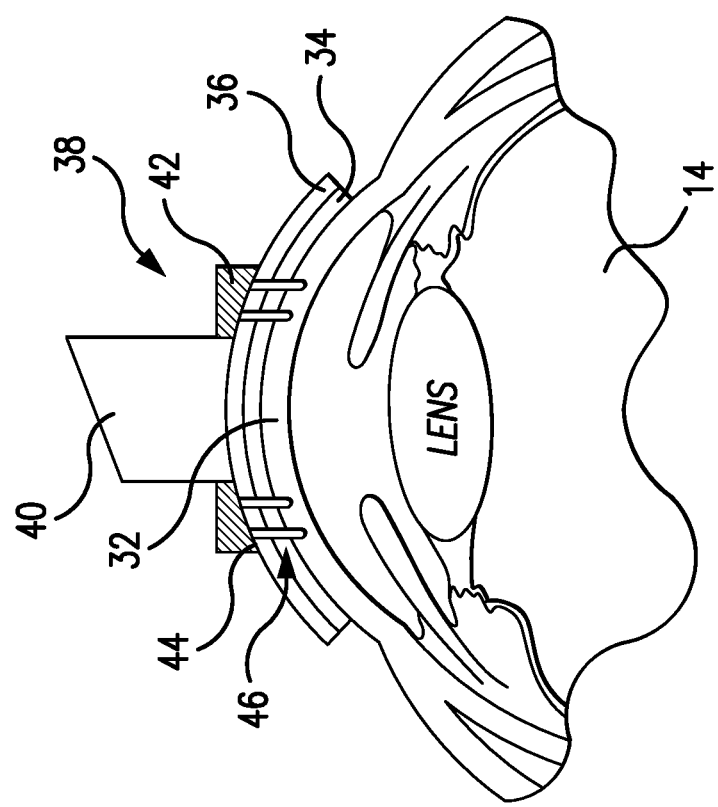
FIG. 2 is a schematic representation of the subject gonioprism contact lens assembly attached to the eye during the surgical procedure.

FIGS. 1A and 1B show schematically the anchoring of the subject suture-free, non-sliding corneal contact lens assembly on the eye during an ophthalmic procedure. As shown in FIG. 1A, the subject cornea contact lens assembly 10 includes a contact lens 12 removeably attached to the eye 14 by means of anchoring system 16 (which will be detailed in further paragraphs). Alternatively, as shown in FIG. 1B, the subject contact lens assembly 10 for ophthalmic procedures includes the contact lens 12 and the contact lens holder 18 which receives the lens 12 and holds the entire system 10 in place during the ophthalmic procedure through the action of the anchoring system 20 on the bottom of the contact lens holder 18.

As shown in FIG. 1A, the anchoring system 16 is formed on the bottom 22 of the contact lens 12 in the form of microstructures 24 which, when brought into contiguous contact with the eye 14, secure the contact lens 12 in place for the duration of the ophthalmic procedure.

As shown in FIG. 1B, the anchoring system 20 is configured on the bottom 26 of the contact lens holder 18. The anchoring system 20 is formed with microstructures 28 which, when brought in contiguous contact with the tissues of the eye 14, maintain the contact lens holder 18 in position during the ophthalmic procedure, and thus supports the contact lens 12 at the desired site of operation.

The system 10 is a novel non-sliding corneal contact lens assembly equipped with the suture-free stabilization/anchoring system for vitreoretinal surgery which utilizes the microstructures 24 on the bottom 22 of the lens 12 or the microstructures 28 on the bottom 26 of the ring holder 18. Microstructure 24 may be in numerous shapes, including, for example, micro-pins 30, micro-grips, micro-barbs, micro-needles, or other textured microstructures on the bottom surface of the contact lens 12 or the contact lens holder 18.

For the sake of simplicity and clarity of description, the microstructures 24 and 28 are described, as an example, in reference to the micro-pins 30, although other microstructures on the bottom 22 of the lens 12 or the bottom 26 of the holder 18 are contemplated in the scope of the present invention. After the contact lens 12 is placed on the cornea 32 of the eye 14 and centered, a surgeon applies downward pressure on the contact lens 12, which secures the lens 12 to the cornea 32. The micro-pins 30 extend through a tear film 34 on the surface of the cornea 32 and a viscous coupling agent (solution) used during the procedure when applied to the ocular surface of the eye.

The coupling fluids applied on the surface of the tear film 34 during the procedure may be selected from a group of coupling fluids such as 2% methocel, thiol-tears gel, 1.4% sodium hyaluronate, 0.9% simple saline, and other contact solutions applicable to the purposes of the ophthalmic care using contact lens.

The micro-pins 30 extend through the tear film 34 and the viscous solution film 36 on the surface of the cornea 32, and gently indent into the superficial cornea 32 without injuring it. A friction force is created between the lens' bottom surface and the coupling agent layer 36, as well as superficial corneal layer 32, by the micro-pins 30 indentation into the superficial cornea 32, so that the contact lens 12 or the contact lens holder 18 is temporarily anchored to the cornea 32 for the duration of the ophthalmic procedure. After the ophthalmic procedure has been completed, the contact lens 12 and/or the lens holder 18 is lifted from the eye 14.

Referring to FIGS. 1A and 2, the subject system 10 is also applicable for surgical gonioprism assembly 38 for glaucoma surgery, where a gonioprism contact lens 40 is used to obtain adequate visualization of the critical angle of the peripheral cornea to perform the micro invasive glaucoma surgery (MIGS) which includes implanting the stent or cutting into the trabecular meshwork. Glaucoma surgeons are generally opposed to placing fixation sutures during the glaucoma procedure in order to avoid trauma to the cornea or sclera of the eye. For this reason, the suture free system 38 of the current invention using a gonioprism contact lens 40 is highly desirable for use in ophthalmic procedures involving glaucoma surgical procedures.

As shown in FIG. 2, the gonioprism contact lens assembly 38 includes the gonioprism contact lens 40 and the lens holder 42. The bottom 44 of the lens holder 42 is formed with microstructure anchoring system 46 which may be in the form of micro-pins, micro-grips, micro-barbs, micro-needles or other textured elements formed on or attached to the bottom surface 44 of the lens holder 42. The details of the gonioprism assembly 38 will be presented in further paragraphs.

Referring to FIGS. 1A-1B, 3A-3B and 4A-4B showing the subject macular contact lens assembly 10, the contact lens 12 may be used by itself or in assembly with the lens holder 18. As presented in FIGS. 1A, 3A, and 4A, the contact lens 12 is used by itself. The contact lens 12 is equipped with the anchoring system 16 configured with microstructures 24 on the bottom 22. The micro-pins (or other microstructures) 30 are strategically placed on the bottom 22 of the lens 12.

Figure 3B:
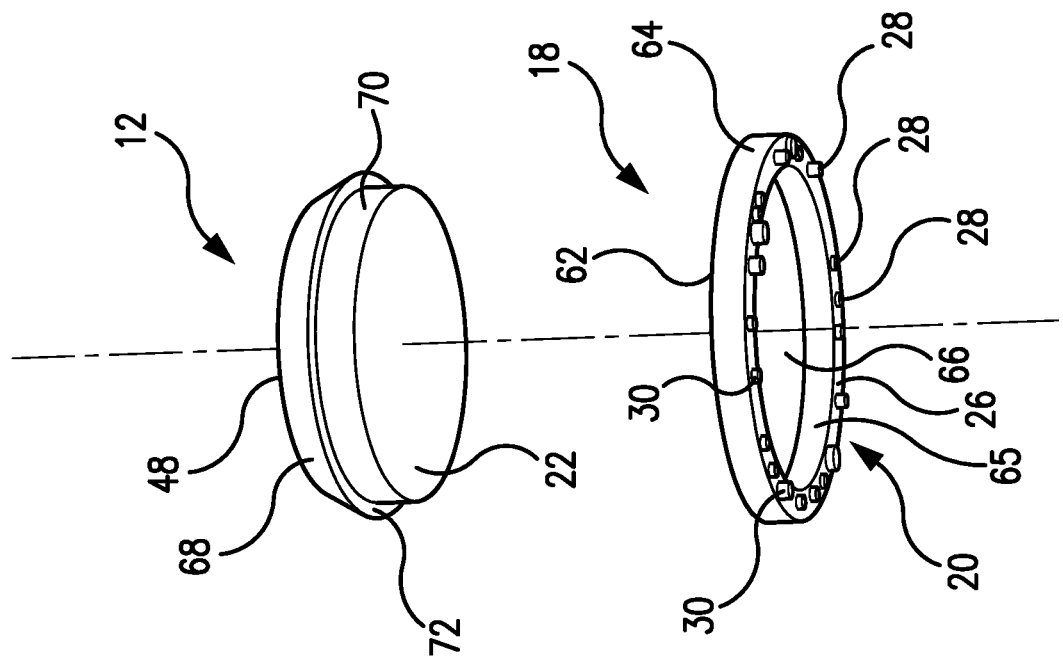
FIGS. 3B and 4B show an exploded view of the subject contact lens and contact lens/holder assembly showing micro structures formed on the bottom of the lens holder, where
Figure 3A:
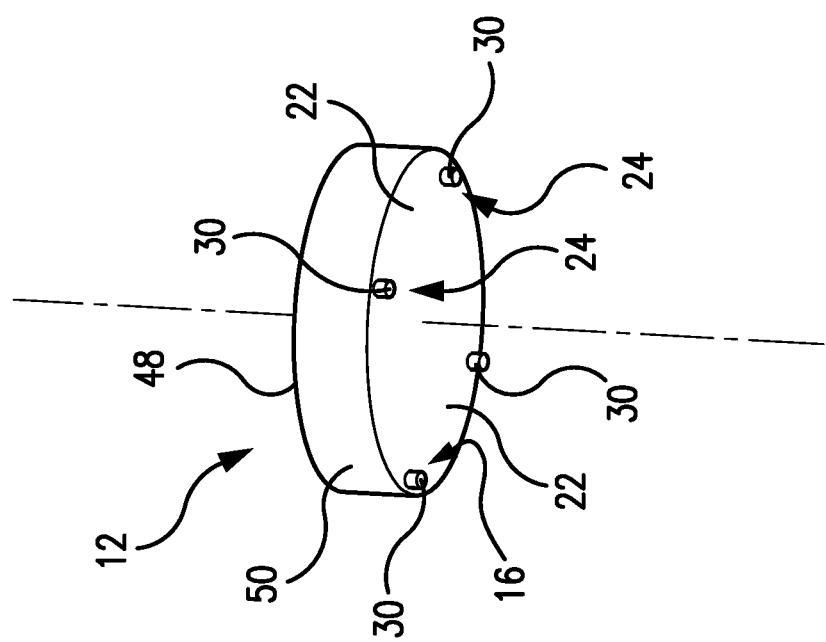
FIGS. 3A and 4A are representative of the subject macular contact lens, where
Figure 4B:
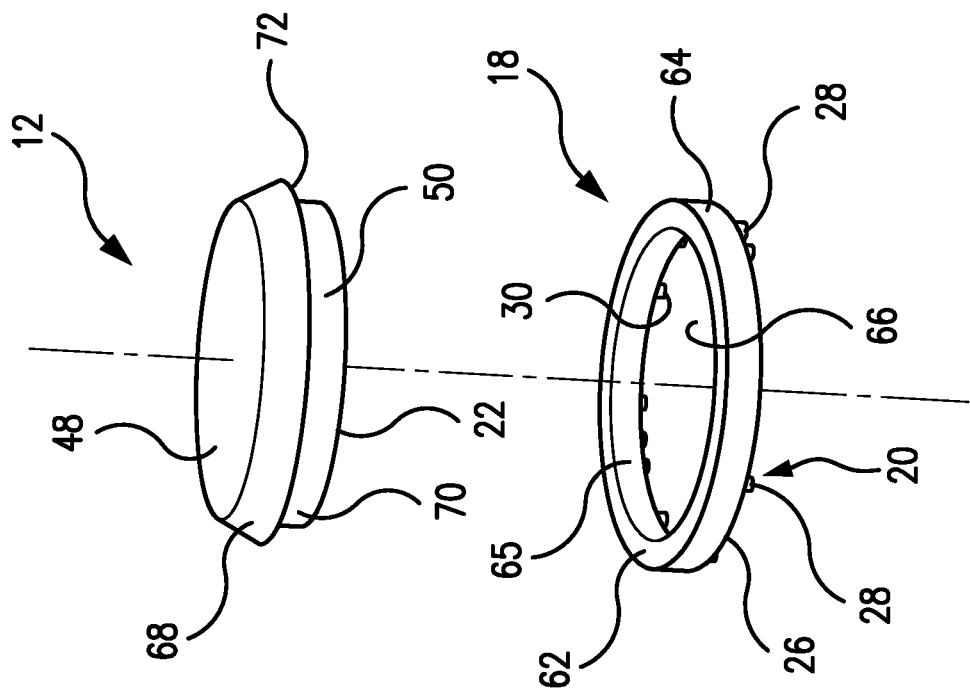
Figure 4A:
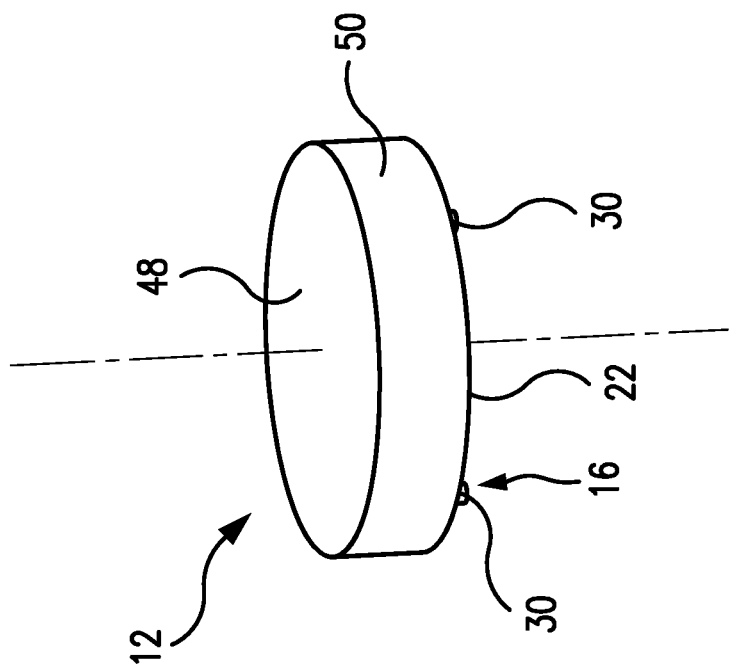

As shown in FIGS. 3A and 4A, the lens' bottom 22 is an eye contacting surface which may be shaped as a circular arc or in another suitable curved configuration to conform with the curvature of the eye cornea 32.

The lens 12 has the upper surface 48 spaced from the bottom surface 22 by circumferentially extending walls 50. The walls 50 of the contact lens 12 may form a cylindrical surface, trapezoidal surface, or other contoured surface as needed for specific optical properties of the lens 12. The upper surface 48 of the lens 12 may be smaller than, larger than, or of the same size with the surface of the bottom 22 of the lens 12 (as dictated by the needed optical properties of the lens 12).

The contact lens 12 may be manufactured from acrylic, glass, or other bio-compatible and optically viable materials used for the contact lens.

A number of micro structured elements 24 are provided on the bottom 22 of the lens 12. The function of the microstructures 24 is to provide friction between the bottom 22 of the lens 12 and the cornea 32 in order to prevent sliding of the lens 12 from the desired surgical site, as well as to anchor the lens in place when the microstructures 24 (for example micro-pins 30) penetrate through the viscous solution film 36 and tear film 34 and anchored to the superficial surface of the cornea 32.

A number of micro-pins 30 are shown on the bottom 22 of the lens 12 which constitutes an anchoring system 16. Although the number of micro-pins 30 shown in FIG. 3A on the bottom 22 of the lens 12 is four, any other number greater than two may be used and is contemplated within the scope of the subject invention.

The micro-pins 30 may be manufactured from surgical steel, bio-compatible plastics or polymers, for example, PEEK (polyether ether ketone), or other bio-compatible materials.

The micro-pins 30 may be manufactured integral with the bottom 22 of the contact lens 12 (for example, by 3-D printing), or may be attached to the bottom 22 of the lens 12 via numerous mechanisms, including, for example, but not limited to, drilling, pressing, threaded engagement, thermo-soldering, coupling with the help of bonding agents (glue, adhesive), various interlocking mechanisms, such as, for example, interlocking tab and groove locking mechanism, etc. The microstructures may also be formed by chemical etching, chemical vapor deposition, plasma machining, photolithography, and other applicable processes.

Figure 5A:
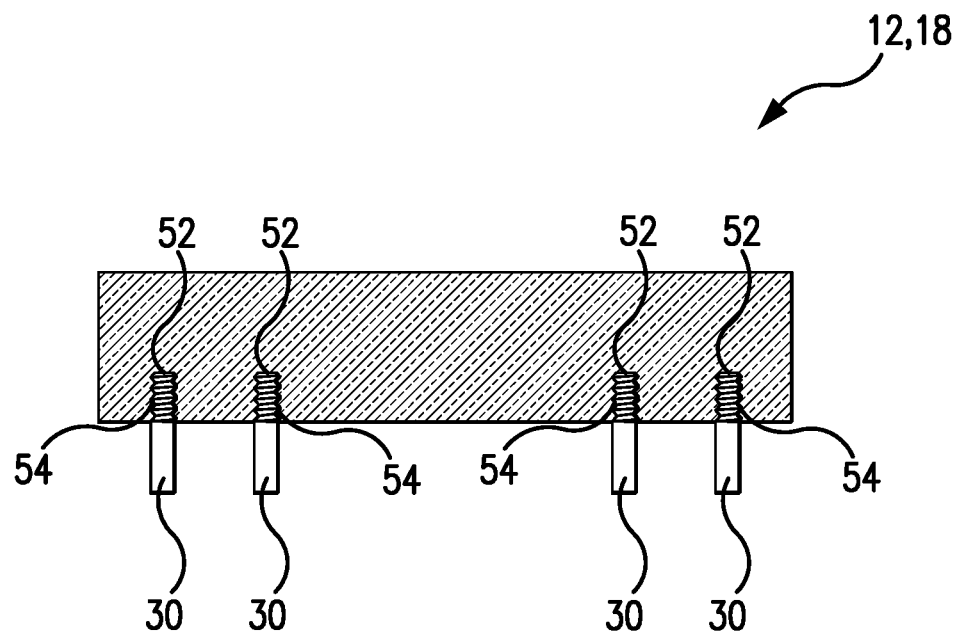
FIG. 5A shows a cross sectional view of the subject contact lens and contact lens/holder assembly showing microstructures threadingly engaged with the subject contact lens.
Figure 5B:
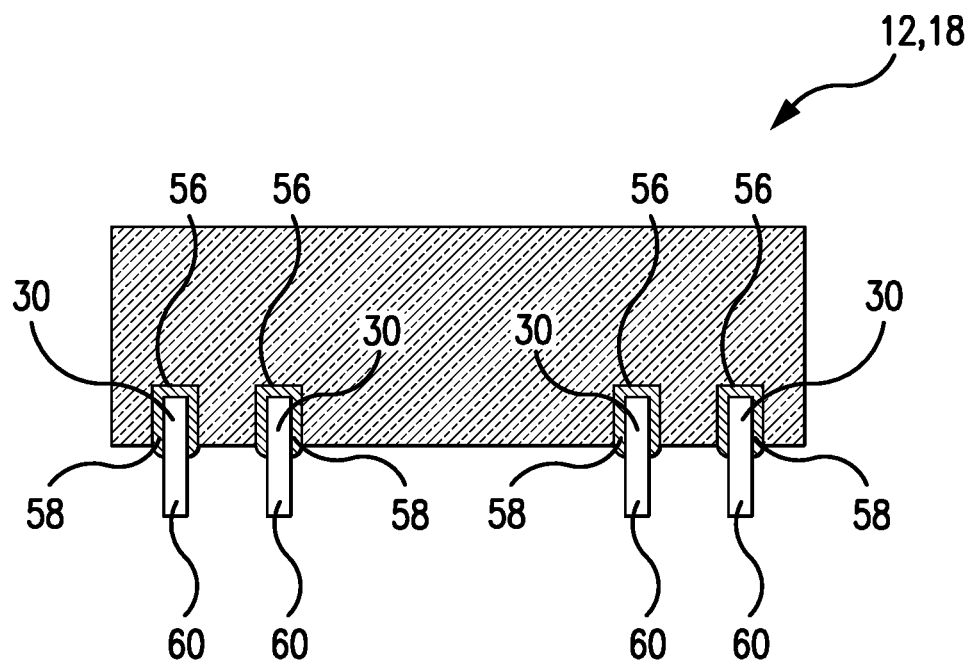
FIG. 5B shows a cross sectional view of the subject contact lens and contact lens/holder assembly showing microstructures fixedly engaged with the subject contact lens with a glue.

For example, as shown in FIG. 5A, openings 52 with the threaded walls 54 are pre-machined at the bottom 22 of the lens 12 to threadingly receive the micro-pins 30. Alternatively, as shown in FIG. 5B, the micro-pins can be glued in the openings 56 with glue 58 which may be, for example, a UV activated epoxy, or any other bio-compatible adhesive material.

Also alternatively to the drilling or gluing the micro-pins 30 into the bottom 22 of the lens 12, the lens with the micro-pins (or other microstructures contemplated in the present invention for the purposes of stabilization, centralization, and prevention of the slipping of the lens from the desired surgical site) may be formed by a 3-D printer from a bio-compatible plastic, or like composition, for example, PEEK material.

The preferred diameter of the micro-pins (in their cross-section) may be in the range of 0.0012 inch, and can protrude from the surface of the bottom 22 of the lens 12 approximately 0.0013 inch to extend through the tear film 34 and viscous solution film 36 into contact with the cornea 32. The micro-pins length from the bottom 22 to the exposed ends 60 thereof generally should not exceed 1 mm in order to prevent deep penetration into the cornea further than the corneal superficial layer.

The cross section of the micro-pins can be tapered down at the exposed ends 60 of the micro-pins 30, or squared off.

Although shown as the same shape and same length in FIGS. 3A and 4A, the microstructures 24 also can be made of different shape and different dimensions, for example, as shown in FIG. 3B.

Referring to FIGS. 1B, 3B and 4B, the ophthalmic contact lens assembly 10 of the present invention includes the lens 12 and the lens holder 18. In this arrangement, the stabilization, as well as centralization, of the ophthalmic contact lens system 10 at the desired site on the eye is provided by the anchoring system 20 configured on the bottom 26 of the lens ring holder 18. As shown, the annular bottom surface 26 of the lens holder 18 includes microstructures in the shapes of micro-pins 30, micro-grips, micro-barbs, micro-needles, or other textured micro-elements 24 positioned at a number of locations on the bottom 26 of the lens holder 18 around the periphery of the lens holder 18.

The annularly shaped contact lens holder 18 has an annularly shaped bottom 26 (with concentrically spaced apart inner and outer peripheral edges) and an annularly shaped upper surface 62 (with concentrically spaced apart inner and outer peripheral edges). The circumferential outside walls 64 extend between the outer peripheral edges of the bottom surface 26 and the outer peripheral edges of the upper surface 62.

Internal walls 65 extend between inner peripheral edges of the annularly shaped bottom surface 26 and upper surface 62, respectively, of the holder 18, and define a circularly shaped opening 66 therebetween.

The macular contact lens 12 is equipped with a flange element 68 which is formed integrally therewith or attached to the outer surface 70 of the circumferentially extending walls 50 of the lens 12. The flange element 68 has a flange 72 extending from the outer surface 70 of the circumferential extending walls 50 of the lens 12.

The bottom surface 22 of the lens 12 and the circumferentially shaped holder opening 66 of the lens holder 18 are shaped and dimensioned to correspond each to the other to permit the bottom 22 of the lens 12 to pass through the circumferentially shaped holder opening 66. The flange member 68 is positioned around the outer surface 70 of the circumferentially extending walls 50 of the lens 12 a distance from the bottom 22 of the lens 12 corresponding to the height of the walls 64 of the lens holder 18 between the bottom surface 26 and the upper surface 62 thereof. When the contact lens 12 is received in the holder opening 66 of the lens holder 18, the flange 72 of the flange member 68 is supported by the annularly shaped upper surface 62 of the lens holder 18, thus preventing the contact lens 12 from displacing its bottom surface 22 below the bottom surface 26 of the lens holder 18.

During the procedure, the lens ring holder 18 is positioned over the cornea 32, and the lens 12 is received in the holder opening 66 of the lens holder 18. The surgeon gently pushes down the contact lens/holder assembly 10, so that the microstructures 28 on the bottom surface 26 of the lens holder 18 penetrate through the tear film 34 and viscous solution film 36 (as shown in FIGS. 1B and 2) and into the contact with superficial layer of the cornea 32 to gently indent into the cornea 32 without traumatizing the eye tissues to provide stabilization and centralization of the contact lens/holder assembly 10 in place and to prevent the deviation of the assembly 10 from the desired position during the ophthalmic procedure.

The lens ring holder 18 may be formed from polyether ether ketone (PEEK) material, or any other compound which is bio-compatible and capable of holding the contact lens 12 in position.

The height of the walls 64 of the lens holder 18 may be in the range of 1-2 mm, with the holder opening diameter ranging from 9 to 15 mm, for example, 11.5 mm.

The microstructures 28, for example, micro-pins 30, are formed along the circumference of the annularly shaped bottom 26 of the lens holder 18 in any manner similar to that described in previous paragraphs for the anchoring system 16 on the bottom 22 of the contact lens 12.

A number of the micro-pins 30 on the bottom 26 of the lens holder 18 may range from 2 to 25 depending on the friction needed between the lens holder 18 and the tissues of the eye.

It has been experimentally concluded that the microstructures 24, 28 can extend from the bottom of the lens 12 or from the bottom of the lens holder 18 no more than 1 mm in order to prevent excessive penetration and possible trauma to the surface of the tissues of the eye under surgery.

Figure 7A:
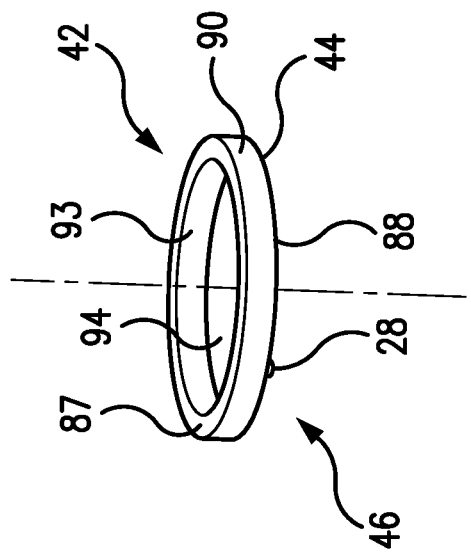
Figure 6A:
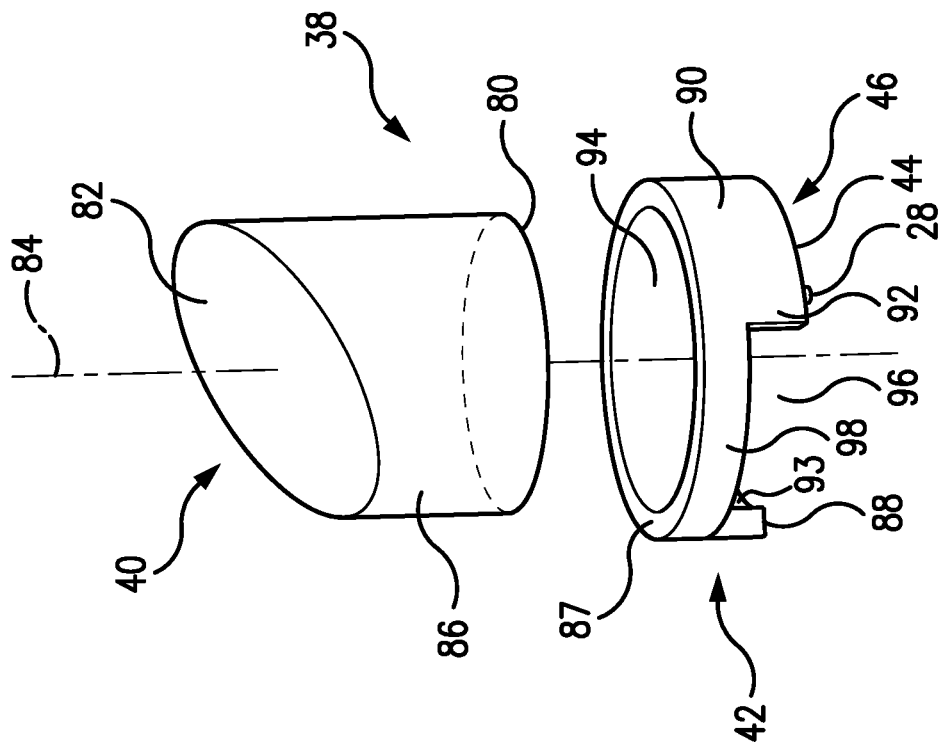

Referring to FIGS. 6A and 6B, as well as FIGS. 7A and 7B, the gonioprism assembly 38 includes a gonioprism contact lens 40 having a bottom surface 80 which is a circularly shaped surface configured to comply with the curvature of the eyeball. The gonioprism contact lens 40 has an upper surface 82 which is oval shaped and tilted as inclined with respect to the longitudinal axis 84 of the gonioprism contact lens 40. Walls 86 extend in cylindrical contoured configuration between the edges of the bottom surface 80 and upper surface 82 of the gonioprism contact lens 40.

The lens holder ring 42 includes an upper annularly shaped surface 87 and a bottom surface 88 which extend each from the other by a predetermined distance 90 defined by circumferentially shaped outer walls 92 of the gonioprism lens holder ring 42. The outer walls 92 extend between the outer peripheral edges of the annularly shaped upper and bottom surfaces 87, 88, respectively.

The lens holder ring 42 further has inner walls 93 which extend circumferentially between inner peripheral edges of the annularly shaped upper and bottom surfaces 87, 88, respectively.

The inner walls 93 are contoured with a cylindrically shaped surface and define a holder opening 94 therebetween. The holder opening 94 in the lens holder ring 42 is shaped and dimensioned to correspond to the bottom surface 80 of the gonioprism contact lens 40.

The circumferentially shaped outer walls 92 and inner walls 93 may be configured with an incision access cut-out 96 which may be a partial cut-out with a connecting element 98 extending along the edge of the upper surface 86 of the lens holder ring 42.

Alternatively, as shown in FIGS. 7A and 7B, the lens holder ring 42 for the gonioprism assembly 38 may be similar to the lens holder 18 shown in FIGS. 3B and 4B formed as an annularly shaped lens holder with an opening 94 shaped and dimensioned for passing the bottom 80 of the gonioprism contact lens 40.

In the arrangement shown in FIGS. 6A and 6B, the partial cut-out 96 is formed for surgical access/entry and visualization of the corneal incision. This cut-out 96 is positioned in relation to the site of the surgery so that the cut-out 96 is stabilized over the corneal or cataract incision. The modification of the gonioprism contact lens assembly 38 shown in FIGS. 6A and 6B permits the surgeon to view the incision site and to guide the surgical instrument into the anterior chamber of the eye for the ophthalmic surgery such as glaucoma surgery.

In the gonioprism assembly 38, shown in FIGS. 6A-6B and 7A-7B, the bottom surface 88 of the lens holder ring 42 is provided with microstructured anchoring system 46 which, similar to that provided at the bottom 22 of the contact lens 12 and the bottom 26 of the lens ring holder 18 shown in FIGS. 1A-1B, 3A-3B and 4A-4B, is manufactured with microstructures 28, described in previous paragraphs.

Figure 8A:
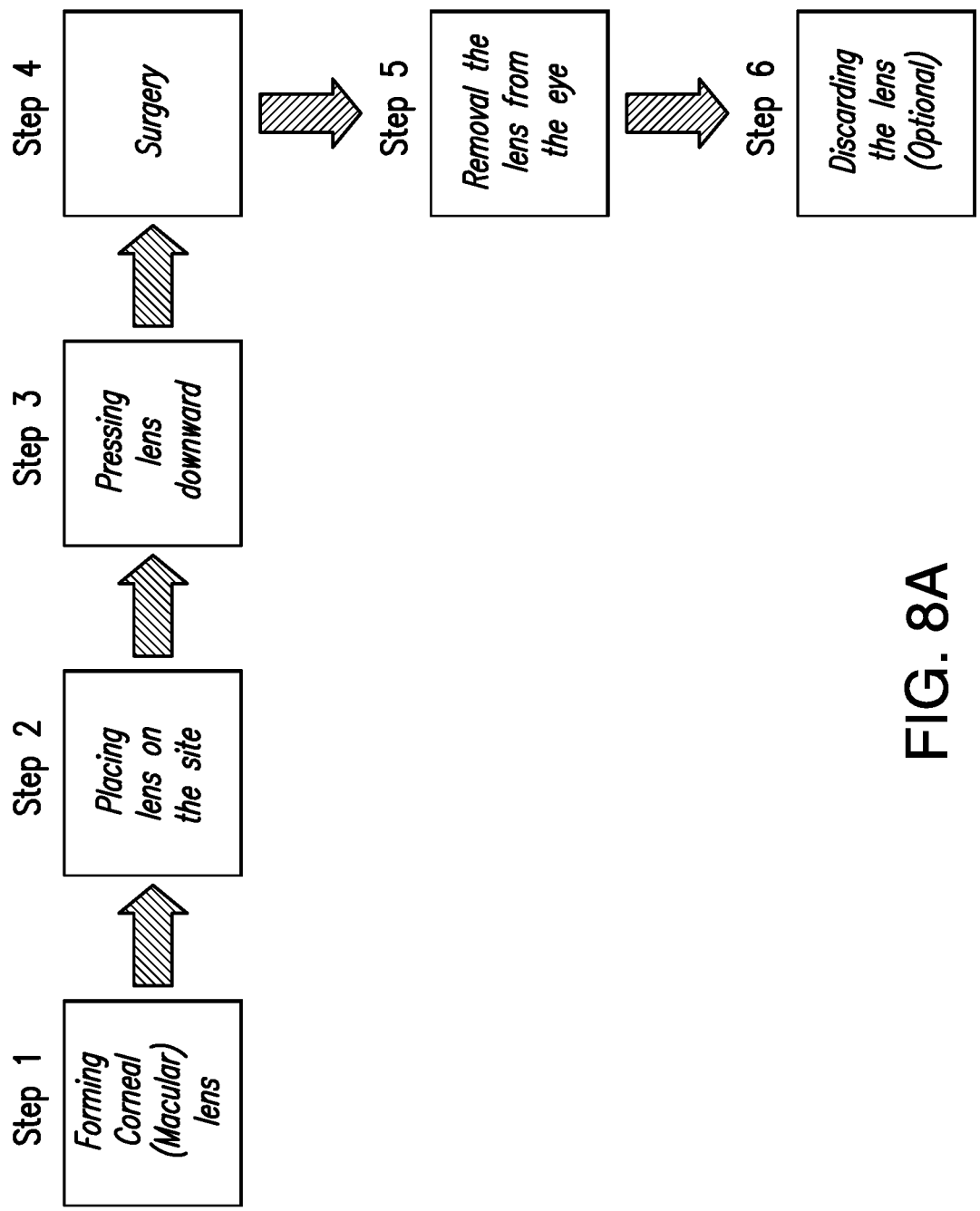
FIGS. 8A-8B represent the steps of the subject surgical procedure using the subject contact lens assembly with the macular (corneal) contact lens (FIG. 8A) and with the gonioprism contact lens assembly (FIG. 8B).

Referring to FIG. 8A, representative of the ophthalmic procedure supported by the use of the subject non-sliding, non-sutured hands-free contact lens anchoring assembly, the method begins in Step 1, wherein the subject corneal (macular) contact lens assembly is formed which includes either the contact lens or the contact lens and the lens ring holder, where either the bottom of the lens is configured with the microstructure anchoring system or the bottom of the ring holder is configured with the anchoring microsystem. When the subject contact lens assembly is formed in Step 1, the method advances to Step 2 where either the subject contact lens with the anchoring system on the bottom thereof, or the lens ring holder with the microstructured anchoring system on the bottom thereof is positioned above the desired surgery site on the eye.

From Step 2, the operation follows to Step 3, where a surgeon gently presses down either the contact lens to provide that the exposed ends of the micro-pins penetrate through the tear film and the viscous solution film, and in contact with superficial layer of the cornea.

In the procedure which uses the assembly of the contact lens and the lens ring holder, the contact lens is lowered into the opening of the lens ring holder. In both situations, the bottom of the contact lens comes into contact with the viscous solution film (when the solution is used for the procedure) or with the tear film.

In the following Step 4, the surgeon performs the ophthalmic procedure such as vitreoretinal surgery or macular surgery. During the procedure, the subject contact lens assembly allows the surgeon to visualize the macular and other structures of the eye in high magnification. The contact lens assembly remains stabilized and centered on the cornea of the eye and is prevented from slipping from the desired surgical site.

Upon completion of the surgery procedure in Step 4, the surgeon lifts the contact lens assembly from the eye, thus disengaging the microstructures from the tissues of the eye. The tissues of the eye are not traumatized by the micro-pins engagement therewith.

Following Step 5, the subject assembly may be discarded (optionally) or sent for disinfection for use in other procedures.

During the Step 4, the surgery is performed in a hands-free manner, when the surgeon (or the surgeon's assistant) does not have to manually locate and relocate the contact lens assembly. Non-sutured stabilization and centralization of the subject contact lens assembly and prevention from sliding from the desired surgical site is provided in the present method by the subject anchoring system formed at the bottom of the lens or at the bottom of the lens ring holder.

Figure 8B:
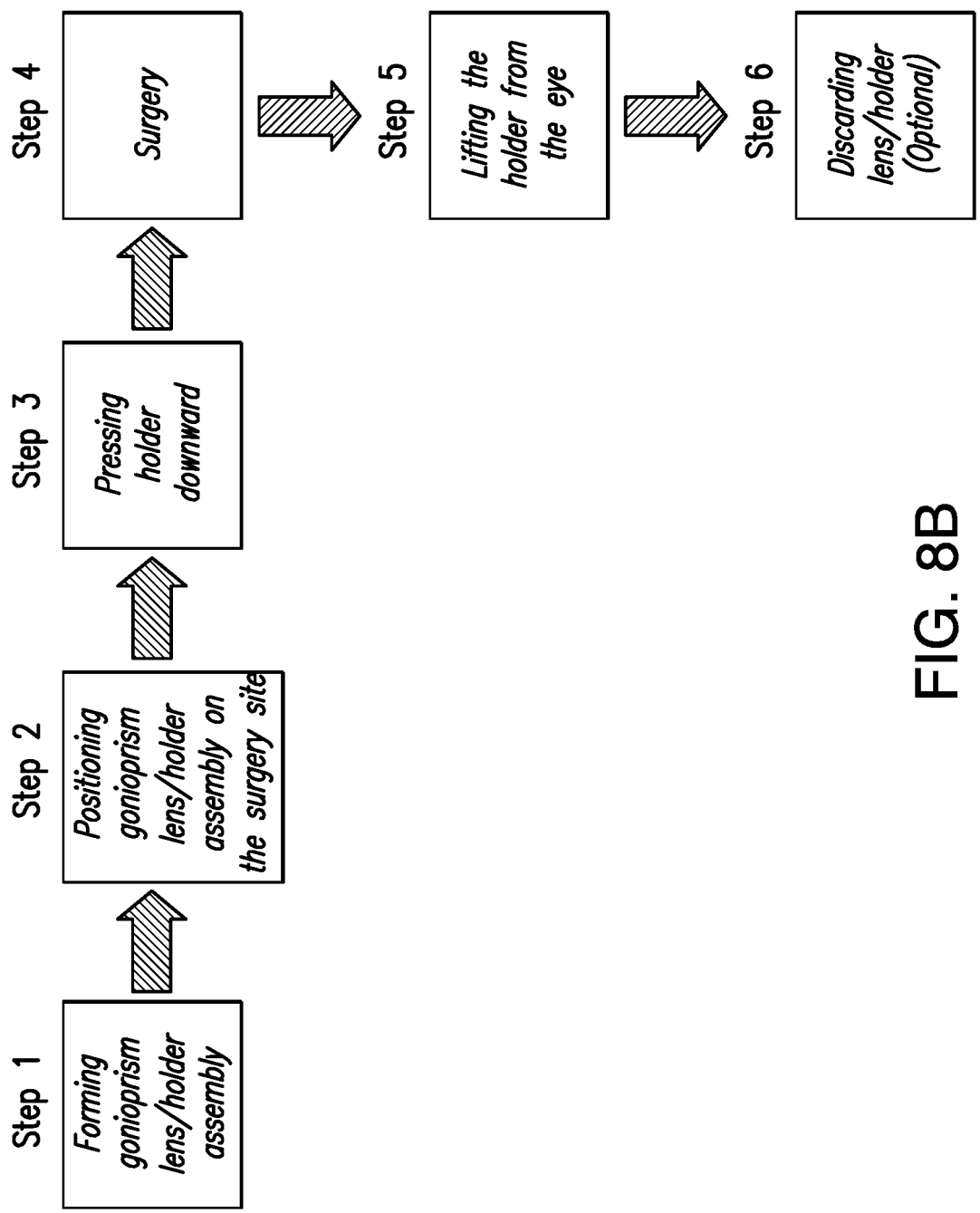

Referring to FIG. 8B, in Step 1, the gonioprism assembly is formed which includes a gonioprism contact lens and the lens holder ring, where a microstructured anchoring system is formed on the bottom of the lens holder ring.

Following Step 1, the surgeon places the lens holder ring of the gonioprism assembly on the site of the surgery, lowers the gonioprism contact lens into the holder opening of the lens holder ring, and in Step 3 gently presses the lens holder ring down into the eye so that the exposed ends of the micro-pins (or other microstructures contemplated in the scope of the present invention) penetrate through the tear film and the viscous solution film of the eye as shown in FIG. 2, and are in contact with a superficial layer of the eye tissue.

In Step 2, the cut-out is positioned over the site of the corneal or cataract incision.

In the following Step 4, the surgery (such as, for example, micro-invasive glaucoma surgery) is performed. During the surgery, the surgeon uses the subject gonioprism assembly in a hands-free manner without the need of stabilization and centralization of the gonioprism assembly by sutures. The sliding of the gonioprism assembly from the site of the surgery is prevented by the friction force provided by the microstructure on the bottom of the lens holder ring.

Upon completion of the surgery in Step 4, the surgeon lifts the lens holder ring form the eye, thus disengaging the exposed ends of the microstructures on the bottom surface of the lens holder ring from the eye's tissues.

In Step 6, following the removal of the gonioprism assembly from the eye, the gonioprism assembly can be optionally discarded or sent for cleaning and treatment for possible use in other procedures.

During an opthalmic procedure, it is important that that the contact lens be maintained in a stable, non-moveable positional location as the surgeon is operationally proceeding. In some cases the patient may tilt his/her head with a responsive tilting of the contact lens holder and the contact lens. This tilting causes unwanted gravitational assist forces to be applied to the contact lens and the contact lens holder which may, in some cases permit a displacement of the contact lens from the intended site.

Figure 9:
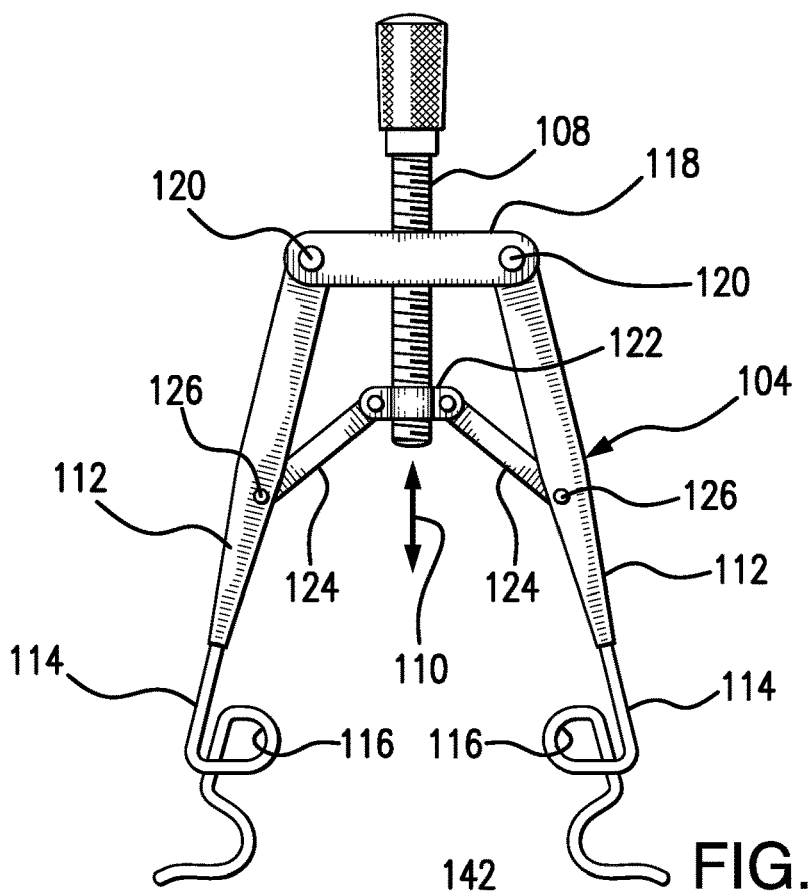
FIG. 9 is a frontal elevation view of an eye speculum used in conjunction with the subject contact lens and contact lens holder.
Figure 10:
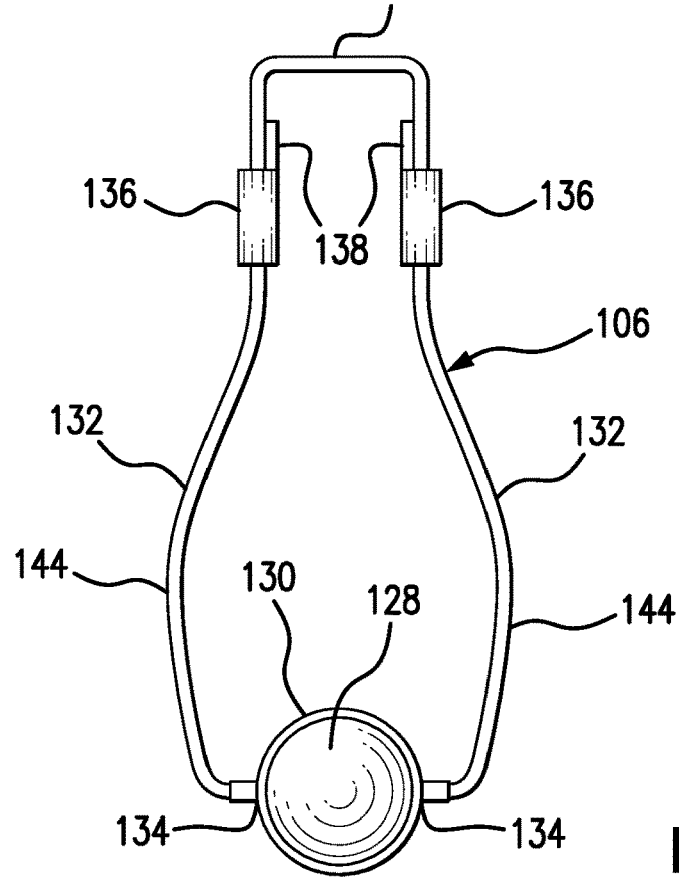
FIG. 10 is frontal elevational view of a stabilization mechanism to be coupled to the eye speculum as seen in FIG. 9.
Figure 11:
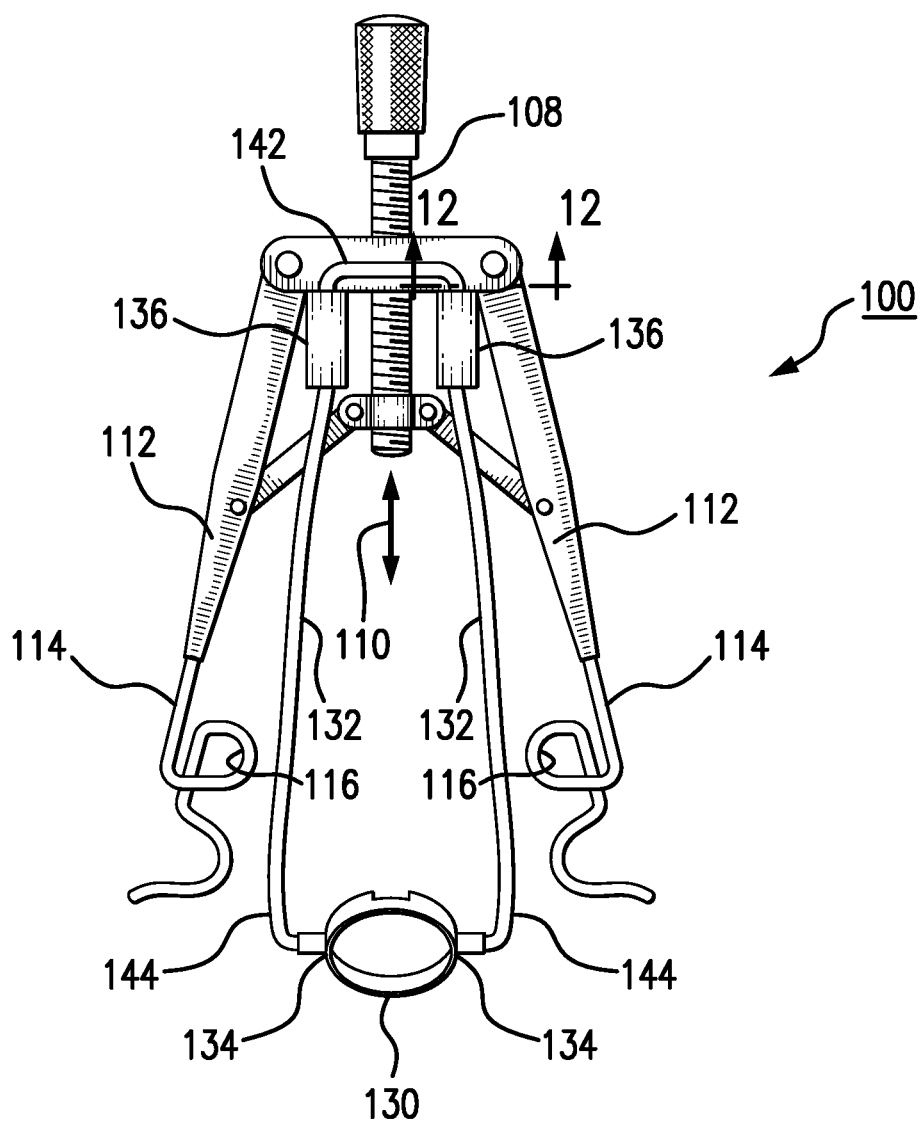
FIG. 11 is a frontal elevational view of the speculum assembly showing the stabilization mechanism in assembly with the speculum.

Referring now to FIGS. 9-12, there is shown a speculum assembly 100 to add further stabilization and non-displaceabilty of the contact lens 128 and the contact lens holder 130 which is seen in the operational combination in FIG. 11.

The contact lens assembly of 100 includes a speculum of 104 seen in FIGS. 9 and 11. Contact lens assembly or speculum assembly 100 includes speculum 104 and stabilization mechanism 106 to be further described in following paragraphs. Speculum or eye speculum 104 may be a standard eyelid speculum used for ophthalmic procedures which is commercially available and commonly known in the art. Speculum 104 may be of the type of that is commonly known as a "Lieberman eyelid speculum", although other speculums may be used in conjunction with stabilization mechanism 106. For purposes of clarity and ease of understanding the "Lieberman" speculum will be used in further description.

Speculum 104 includes threaded member 108 for threaded engagement with plate member 118 of speculum 104. Operationally, threaded member 108 may be rotationally displaced to displace threaded member 108 in a linear direction coincident with axis line 110. A lower section (as seen in FIG. 9) of threaded member 108 is coupled to bracket 122 which is reversibly displaceable along axis line 110. Bracket 122 is pivotally connected to intermediate arm members 124 positioned on opposing sides of bracket 122 as is seen in FIG. 9.

Intermediate arms 124 are respectively pivotally connected at pivots 126 to speculum arm members 112. Speculum arm members 112 are pivotally coupled to plate member 118 on opposing horizontally displaced ends to permit radial displacement of speculum arm members 112 responsive to the rotation of threaded member 108.

In this manner, rotation of threaded member 108 which is in threaded engagement with plate member 118 causes a linear displacement in axis direction 112 of bracket member 122. Displacement of bracket member 122 being pivoted to intermediate arm members 124 which are in themselves pivoted being radially displaceable.

Loop members 114 are fixedly connected to respective speculum arm members 112 as shown. Loop members 114 are operationally used for bearing against the patient's eyelids to maintain the patient's eyelids displaced each from the other during the ophthalmic procedure. As speculum arm members 112 are radially displaced away from each other there is a respective displacement of loop members 114 away from each other. As previously described loop members 114 are adapted to contact opposing eye lids of a patient during the medical procedure and maintain the patient's eyelids in a relatively stable and spaced position.

Loop members 114 are generally wire members composed of a biocompatible solid material which has some flexibility such as stainless steel or some like composition not important to the inventive concept as herein described with the exception that loop members 114 are capable of accepting the loads imposed thereon.

Contact lens assembly 100 includes contact lens 128 which may in some cases be in the form of a geoprism lens as shown in FIG. 10. Contact lens holder 130 as seen in FIGS. 10 and 11 is secured to a contact lens 128 through adhesive bonding or some other like technique. Contact lens holder 130 is fixed to contact lens 128 at least partially along a periphery of contact lens 128. In this manner contact lens holder 128 is fixedly attached to to contact lens 128. The function of contact lens holder 130 is to provide support and stabilization of contact lens 128 when contact lens 128 is positioned over a medical procedure site of a patient's eye.

Contact lens 128 may be of the type previously described in FIG. 3A-4B. Contact lens 128 may include the anchoring mechanisms previously described to retain contact lens 128 at the selected procedure site during the ophthalmic procedure. Such an anchoring mechanism as previously described may include a plurality of microstructures located on the bottom surface of wall contact lens 128. These microstructures may be selected from the group of micro-pins, micro-grips, micro-barbs, micro-needles, textured micro-elements as well as combinations thereof.

As described, contact lens holder 130 is fixedly secured to contact lens 28 throughout or at least a portion of the periphery of contact lens 130 as is seen in FIG. 10. Contact lens holder 130 may be formed of a polygonal or circular cross-sectional contour tubing for matingly interfacing with contact lens 128. As shown in FIGS. 10 and 11 contact lens holder 130 is formed by a substantially cylindrical tubing which receives contact lens 128. However, the particular contour of contact lens holder 130 is not important to the inventive concept as herein described with the exception that it is adhered to at least a portion of contact lens 128 in order to securely hold contact lens 128 within contact lens holder 130. Contact lens holder 130 may be composed of a solid composition which is bio-compatible, such as stainless steel or some like composition which is substantially rigid.

As more clearly seen in FIG. 10, stabilization mechanism 106 includes flexible stabilization wire 132 having a stabilizing wire first ends 134 secured to contact lens holder 130 on opposing sides of lens holder 130 as is shown in both FIGS. 10 and 11. Stabilizing wire first ends 134 may be adhered to lens holder 130 by adhesion or some like technique with the important consideration being that lens holder 130 is secured to stabilizing wire 132 at stabilizing wire first ends 134. When taken in combination, contact lens 128, contact lens holder 130, and flexible stabilizing wire 132 form a closed contour.

Stabilizing wire 132 passes through a pair of sleeve members 136 which are mounted to and on opposing sides of stabilizing wire 132 which is clearly seen in FIG. 10. Each of sleeve members 136 is formed of either an elastic composition such as rubber or in fact may be a formed of a bio-compatible composition which may be rigid. For purposes of illustration, sleeve member 136 is shown as being a substantially tubular contour. Sleeve members 136 are fixedly attached to stabilizing wire 132 by adhesive attachment or some like mechanism not important to the inventive concept as herein described. Each sleeve member 136 includes a respective sleeve member appendage or lug 138 extending from end of each of sleeve members 136 in the axial direction 110. Sleeve member appendages 138 are fixedly secured to sleeve members 136 by being formed in one-piece formation with the sleeve members 136 or otherwise fixedly attached to respective sleeve members 136.

Each end of plate member 118 is formed with a recess 140 within which respective speculum arm members 112 are pivotally connected as previously described. Thus the ends of plate member 118 take the form of a C-shape which provides a space between the speculum arm members 112 and the body of plate member 118.

Figure 12:
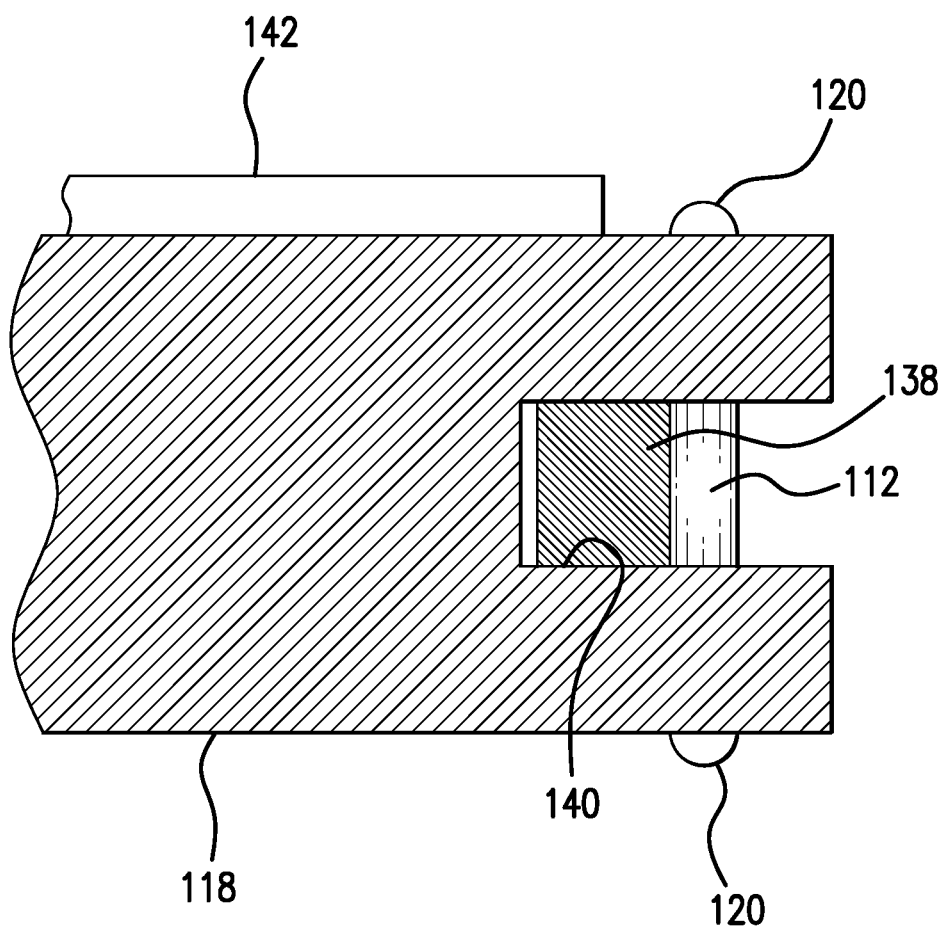
FIG. 12 is a cross-sectional view partially cut-away showing the sleeve member appendage inserted within a plate member of the speculum.

Sleeve member appendages 138 extending from an end of each of sleeve members 136 are insertable within opening or recess 140 of plate member 118 as seen in FIG. 12. Sleeve member appendages 138 are inserted within plate opening 140 and may be wedged within plate opening 140 or otherwise secured thereto. In one aspect of system 100, appendages or lugs 138 are frictionally secured within recesses 140 to permit easy removal of stabilizing mechanism 106 from eye speculum 104 subsequent to the ophthalmic procedure. Stabilizing wire 132 includes stabilizing wire upper section 142 and is adapted to extent over an upper surface of plate member 118 in a direction perpendicular to axis direction 110.

In this manner there is formed a continuous stabilizing wire 132 contour extending from stabilizing wire first ends 134 to provide a continuous stabilizing wire 132 between stabilizing wire first ends 134 as is seen in both FIGS. 10 and 11.

Stabilizing wire 132 includes a lower stabilizing wire section which passes between loop members 114 having inner loop sections 116 as is seen in assembly in FIG. 11.

Operationally, when threaded member 108 is rotated, respective intermediate arm members 124 radially displace speculum arm members 112. Stabilizing wire 132 is mounted within speculum arm members 112, as is seen in FIG. 11 in operational combination. Stabilizing wire 132 is thus secured to eye speculum 104 between the displacement distance of inner loop sections 116 and may be essentially independent of the displacement of speculum arm members 112.

Stabilizing wire 132 is fabricated from a malleable material such as stainless steel, a plastic composition or some like material which can hold its shape in a stable mode, but can be bent or flexibly displaced.

In this manner during an ophthalmic procedure, contact lens holder 130 and captured contact lens 128 are lowered onto the predetermined location desired in cooperation with the eye speculum 104. If adjustments are needed to the positioning of lens holder 130, the surgeon can simply apply pressure to a mid-section of stabilizing wire 132 to effect displacement of lens holder 130 and associated contact lens 128. The adjustment pressure on stabilizing wire can be accomplished by the surgeon applying displacement force to the stabilizing wire 132 through the use of forceps contacting and applying pressure to opposing sides of stabilizing wire 132.

In this manner, when a patient during a medical procedure tilts his/her head, the contact lens holder 130 and responsively the contact lens 128 are maintained in a stabilized position which acts against any gravity assist forces which may be encountered during the ophthalmic procedure.

FIGS. 13, 14 and 15A-15C show schematically the subject alternative system 200 for anchoring the corneal contact lens assembly on the eye 204 during an ophthalmic procedure. The present inventive concept is applicable to a wide variety of ophthalmic contact lens. However, as an example only, without restriction of the subject invention scope, the following paragraphs focus on a gonioprism contact lens assembly 206 shown in FIGS. 13 and 15B-15C.

The subject gonioprism contact lens assembly 206 includes a gonioprism contact lens 208 to be removably attached to the eye 204 during an ophthalmic procedure by means of the subject magnetically actuated anchoring system (also referred to herein as the anchoring mechanism or anchoring. stabilizing mechanism) 210, which will be detailed in further paragraphs.

The subject contact gonioprism lens assembly 206 for ophthalmic procedures further includes the gonioprism lens holder 212 which receives the lens 208 and holds the entire gonioprism contact lens assembly 206 in place during the ophthalmic procedure through the action of the anchoring system 210 provided in cooperation with the contact lens holder 212. The anchoring system 210 may be provided in a direct cooperation with the contact gonioprism lens 208 or, alternatively, in a direct coupling with the lens holder 212. As an example only, and not to limit the subject design to such particular configuration, the subject system will be further described with the focus mainly on the embodiment in which the subject anchoring system 210 can be coupled directly to the contact lens holder 212.

The anchoring system 210 is configured with a pair of magnetically cooperating anchoring members (also referred to herein as units) 214 and 216, which may both be fabricated from a magnetic material, or alternatively, one of the anchoring units 214, 216 may be fabricated from a magnetic alloy, while another anchoring unit may be manufactured from a metallic material capable of magnetic attraction to the cooperating anchoring unit.

The subject anchoring mechanism 210 further includes a wire member 218 which is attached at the end 220 thereof to the contact lens holder 212 through a rotational mechanism 222. The rotational mechanism 222 permits a bi-directional rotation of the lens holder 212 about the longitudinal axis 224 of the wire member 218 (shown by arrows A in FIG. 13).

Alternatively, the wire member 218 may be attached directly to the contact gonioprism lens 208. However, as an example only, but not to restrict the scope of the subject invention to this particular design, further description will focus on the design assuming the attachment of the wire member 218 directly to the lens holder 212.

Figure 13:
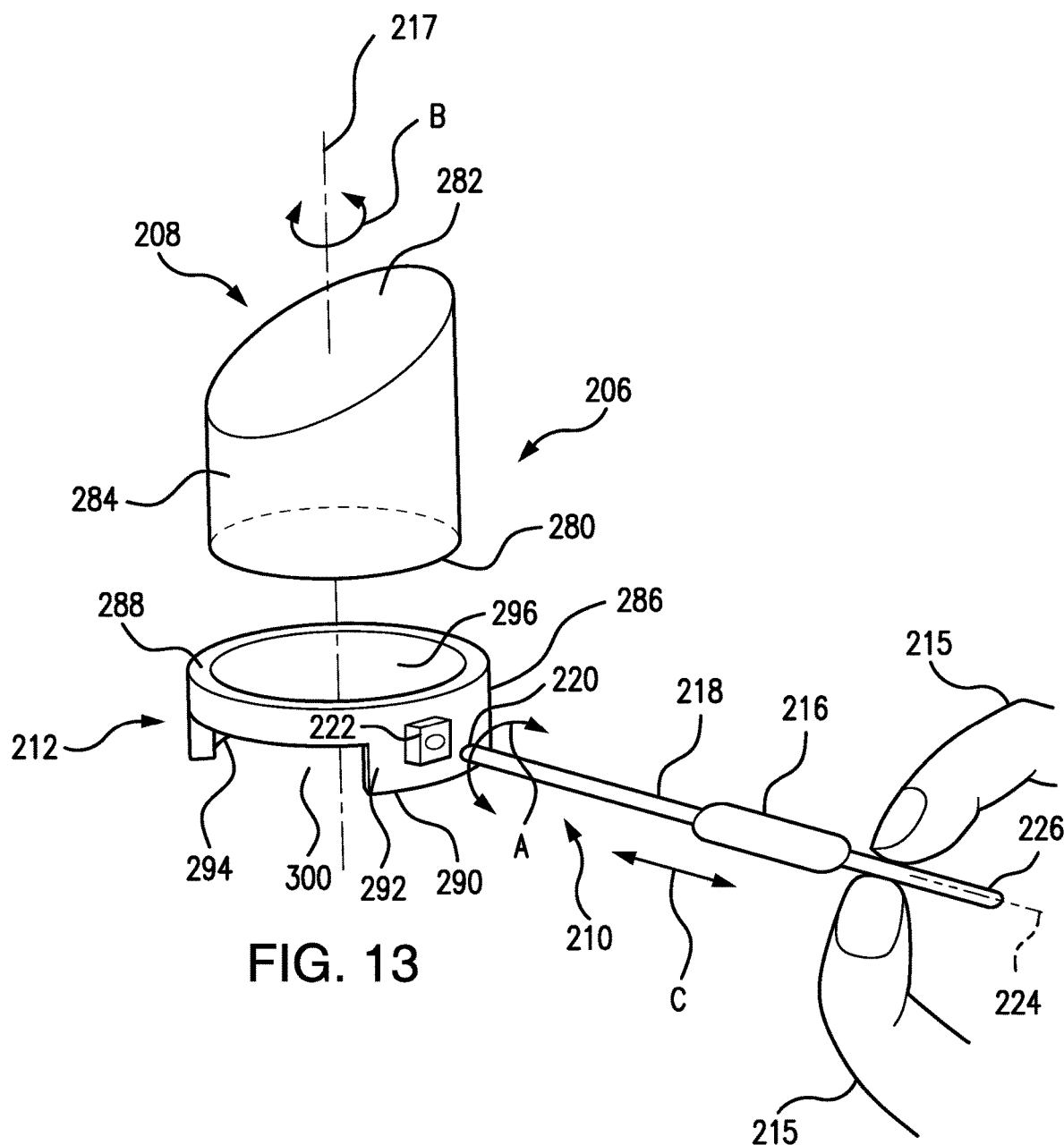
FIG. 13 an exploded view of the subject gonioprism contact lens assembly in an alternative embodiment showing the contact lens holder based magnetically cooperating member of the subject anchoring mechanism.

When the wire member 218 is held by a surgeon with the finger tips 215, for example, in proximity to the end 226 of the wire member 218 (as shown in FIG. 13), during positioning of the contact lens assembly 206 at the operational site, the surgeon can rotate the lens holder 212 (as well as the lens 208 attached thereto) about the longitudinal axis 224 of the wire member 218 to adjust the lens positioning. In addition, the lens 208 can be rotated bi-directionally within the lens holder 212 co-axially with the axis 217 (of the lens and the lens holder) along the arrows B (shown in FIG. 13). The rotational displacement of the lens holder 212 relative the wire member 218, as well as rotational displacement of the lens 208 co-axially within the lens holder 212, provides a sufficient number of degrees of freedom for the contact lens 208 orientation adjustment which is highly beneficial for the lens holder positioning relative to the operational site.

An additional degree of freedom for adjustment of the subject contact lens assembly 206 positioning is beneficially provided by a displacement feature of the lens holder based anchoring member 216 along the wire member 218. The magnetically attractable lens holder based anchoring member 216, as shown in FIG. 13, can be displaced bi-directionally along the wire member 218 in the directions C, as shown in FIG. 13, thereby further promoting the adjustability of the relative positioning of the anchoring members 214 and 216 for an increased preciseness of positional placement and anchoring of the contact lens assembly in place.

The mechanism ensuring the displacement of the anchoring unit (member) 216 along the wire member 218 may be configured either by machining of a through opening within the anchoring member 216 for the wire member 218 to pass through to permit the anchoring member 216 sliding along the wire member 218, or by providing a some sort of a rail structure for the anchoring member 216 displacement along the wire member 218, or, alternatively, by forming a threaded engagement between the anchoring member 216 and the wire member 218 which can be transformed into a linear displacement of the anchoring member 216 along the wire member 218. These and any other configurations permitting displacement of the anchoring member 216 along the wire member 218 are contemplated in the the subject system.

Figure 15A:
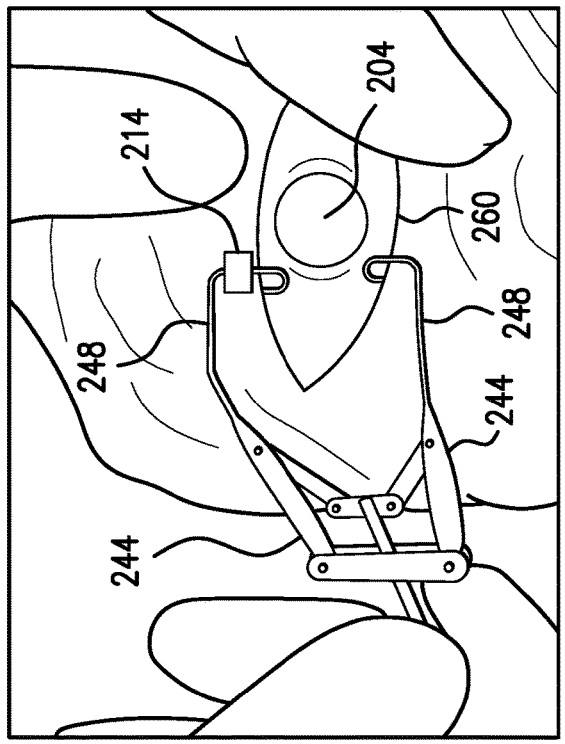
FIGS. 15A-15C illustrate schematically an ophthalmic procedure using the subject alternative embodiment of the gonioprism contact lens assembly with the magnetically actuated anchoring mechanism, where
Figure 15B:
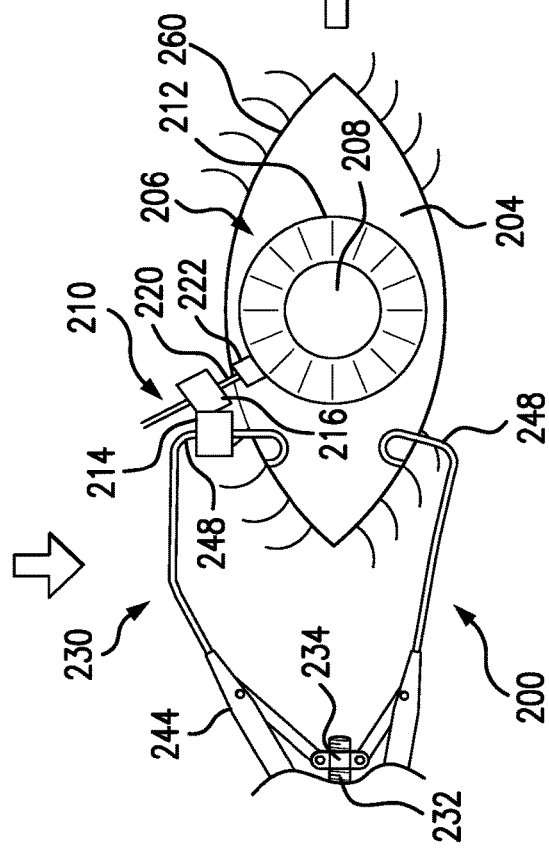

As shown in FIGS. 13 and 15B, the anchoring unit 216 is attached to the wire member 218 at a predetermined distance from the end 220 thereof, and may be positioned in proximity to, or at the opposite end 226 of wire member 218. As was indicated supra, the anchoring unit 216 can be displaced along the wire member 218 between the ends 220 and 226 to adjust position of the contact lens at the operational site.

Figure 14:
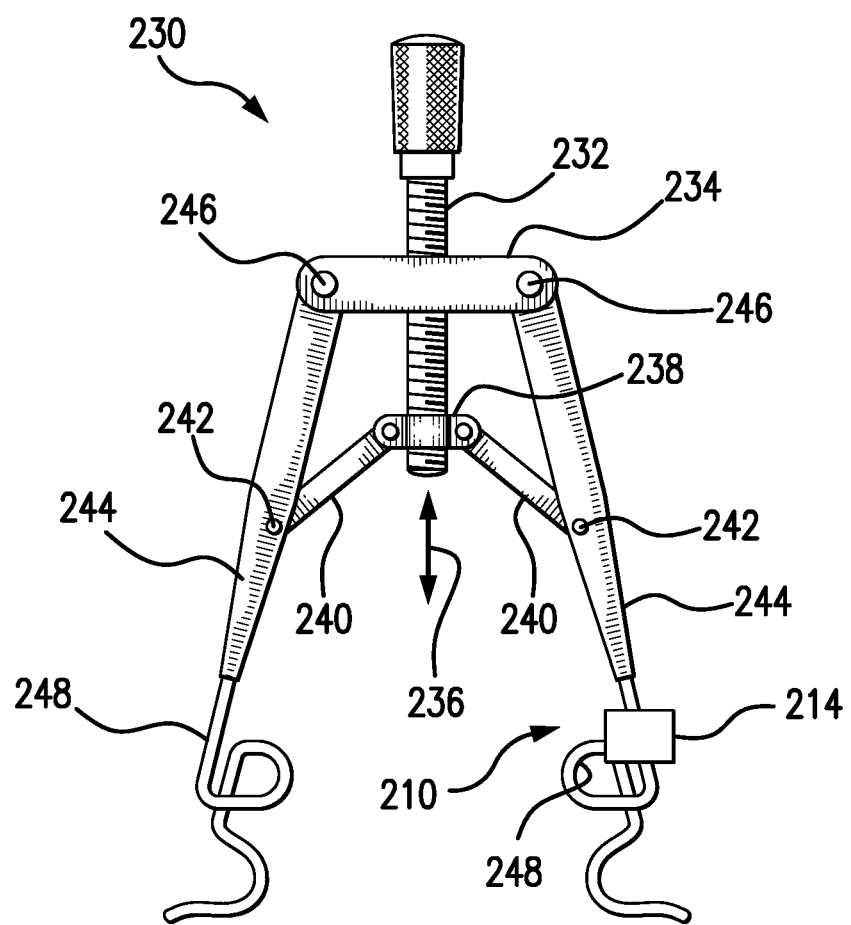
FIG. 14 is a frontal elevation view of an eye speculum modified for usage as a part of the subject anchoring mechanism in conjunction with the subject contact lens assembly.

The subject gonioprism contact lens assembly 206 cooperates with a speculum 230 shown in FIGS. 14 and 15A-15B for realization of the subject anchoring mechanism 210. In order to serve as a contributing element of the subject anchoring system 210, the eyelid speculum 100 shown in FIGS. 9-11 has been modified. The modified speculum 230, as shown in FIGS. 14 and 15A-15B, is equipped with the magnetically attractable anchoring member 214 which may be fabricated either from a magnetic alloy, or a metal material (provided that the anchoring unit 216 is fabricated from a magnetic alloy).

The subject speculum 230 may be fabricated based on any type of the eyelid speculum, for example, the type that is commonly known as a "Lieberman eyelid speculum", although other speculums may be used in conjunction with the subject anchoring mechanism 210 in the subject system 200. For the purpose of clarity and ease of understanding, the "Lieberman" speculum will be used in further description as the basis for the subject speculum modification.

The speculum 230 includes threaded member 232 for threaded engagement with a plate member 234 of the speculum 230. Operationally, the threaded member 232 may be rotationally displaced to displace the threaded member 232 in a linear direction coincident with the axis line 236.

A lower section (as seen in FIG. 14) of the threaded member 232 is coupled to a bracket 238 which is reversibly displaceable along the axis line 236. The bracket 238 is pivotally connected to an intermediate arm members 240 positioned at the opposing sides of the bracket 238 as is seen in FIG. 14.

The intermediate arms 240 are respectively pivotally connected at pivots 242 to the speculum arm members 244. The speculum arm members 244 are pivotally coupled to the plate member 234 at the opposing horizontally displaced ends 246 to permit radial displacement of the speculum arm members 244 responsive to the rotation of the threaded member 232.

In this manner, rotation of the threaded member 232 (which is in a threaded engagement with the plate member 234) causes a linear displacement in the axis direction 236 of the bracket member 238. Displacement of the bracket member 238, being pivoted to the intermediate arm members 240, results in a radial displacement of the arm members 240.

Wire loop members 248 are fixedly connected to respective speculum arm members 244 as shown in FIG. 14. The wire loop members 248 are operationally used for bearing against the patient's eyelids to maintain the patient's eyelids displaced each from the other and stabilized during the ophthalmic procedure, as presented in FIGS. 15A-15B.

As the speculum arm members 244 are radially displaced away from each other, there is a respective displacement of the wire loop members 248 away from each other. The wire loop members 248 are adapted to contact opposing eye lids of a patient during the medical procedure and maintain the patient's eyelids in a relatively stable and spaced position, as shown in FIGS. 15A-15B.

The wire loop members 248 are generally wire structures composed of a biocompatible solid material which has some flexibility such as stainless steel or some like composition not important to the inventive concept, as herein described, with the exception that the wire loop members 248 are capable of accepting the loads imposed thereon.

In the subject system 200, the modified eye speculum 230 is equipped with the magnetically attractable anchoring member 214 (also referred to herein as the speculum-based anchoring unit) which is attached to one of the wire loop members 248.

The subject contact lens assembly 206 is a novel non-sliding corneal contact lens assembly equipped with the suture-free stabilization/anchoring system 210 for vitreoretinal surgery which utilizes the magnetic attraction between the magnetically cooperating anchoring units (members) 214 and 216, where the unit 216 is a lens holder-based anchoring unit attached at the wire member 218 which is rotationally secured to the lens holder 212 (or to the gonioprism lens 208 itself), and where the speculum-based anchoring member 214 is secured to the wire loop member 248 of the eye speculum 230.

In operation, as shown in FIG. 15A, the eyelid speculum 230 is used by a surgeon in the ophthalmic procedure to widen and stabilize the eyelids 260. When the eyelid speculum 230 is applied to the eyelids 260, the anchoring member 214 attached to the wire loop member 248 is placed and remains at the predetermined position on the eyelid 260 of the eye 10 (shown in FIG. 15A).

Subsequently, as shown in FIG. 15B, the surgeon positions the contact lens holder 212 (along with the contact lens 208) on the eye 204, adjusts the positioning of the contact lens on the eye, as well as the position of the anchoring member 216 along the wire member 218, and brings the anchoring member 214 and 216 in contact one with another (after adjusting positional placement of the lens holder-based anchoring unit along the wire member 218). The anchoring members 214 and 216 are magnetically attracted each to the other, and, thus, anchor and stabilize the contact gonioprism lens assembly 206 in a stable position at the operation site in connection with the anchoring member 214 on the eyelid speculum 230 secured to the eyelid 260.

For being magnetically cooperative, the first and second anchoring members 214, 216 are fabricated from magnetically attractable materials selected from a group consisting of a magnetic material/alloy, metal (or ferrous) material/alloy, and their combination, meaning that at least one of the anchoring members is made from a magnetic material, while another can be made from a magnetic material or a ferrous material. For example, when the anchoring member 216 secured to the contact lens holder 212 is fabricated from a magnetic alloy, the anchoring member 214 secured to the eye speculum 230 may be manufactured either as a magnet or as a ferrous plate.

Figure 15C:
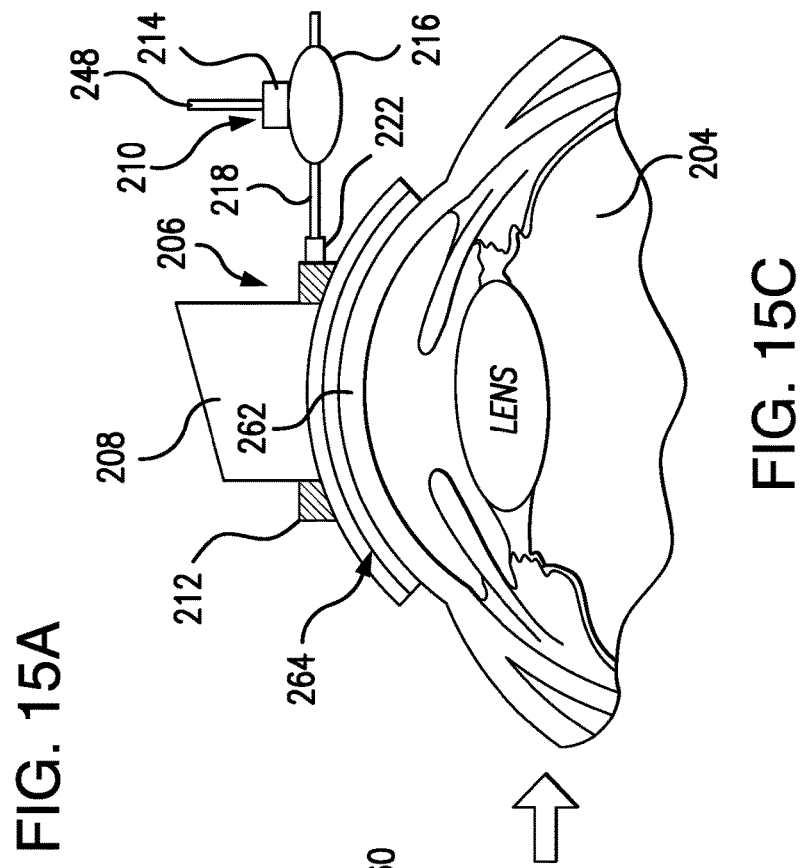

During positioning of the contact lens assembly 206 on the eye 204, the surgeon can beneficially adjust orientation and position of the contact lens holder 212 due to the rotational mechanism 222 formed between the wire member 218 and the contact lens holder 212. After the contact lens assembly 206 is placed on the cornea 262 of the eye 204 and centered, the surgeon, by bringing the anchoring units 214 and 216 in contact one with another, secures the contact lens 208 to the cornea 262, and can perform the ophthalmic procedure in a "hands-free" fashion, as shown in FIGS. 15B-15C.

A viscous coupling agent (solution) 264 is used during the procedure when applied to the ocular surface of the eye, so the bottom of the lens 208 and the lens holder 212 may be in a direct contact with the solution applied on the surface of the eye for reducing sensitivity of the eye surface to the contact with the contact lens at the contact lens holder.

The coupling fluids 264 applied on the surface of the tear film during the procedure may be selected from a group of coupling fluids such as 2% methocel, thiol-tears gel, 1.4% sodium hyaluronate, 0.9% simple saline, and other contact solutions applicable to the purposes of the ophthalmic care using contact lens.

Although applicable to any contact lens and numerous ophthalmic procedures, as an example, the subject system 200 is described in the application for the surgical contact gonioprism assembly 206 for glaucoma surgery, where the gonioprism contact lens 208 is used to obtain adequate visualization of the critical angle of the peripheral cornea to perform the micro invasive glaucoma surgery (MIGS) which includes implanting the stent or cutting into the trabecular meshwork. Glaucoma surgeons are generally opposed to placing fixation sutures during the glaucoma procedure in order to avoid trauma to the cornea or sclera of the eye. For this reason, the subject suture-free system 200 of the current invention using the gonioprism contact lens 208 is highly desirable for use in ophthalmic procedures involving glaucoma surgical procedures.

A bottom 280 of the contact lens 208 is an eye contacting surface which may be shaped as a circular arc or in another suitable curved configuration to conform with the curvature of the eye cornea 262.

The gonioprism lens 208 has the upper surface 282 spaced from the bottom surface 280 by circumferentially extending side walls 284. The walls 284 of the contact lens 208 may form a cylindrical surface, trapezoidal surface, or other contoured surface as needed for specific optical properties of the lens 208. The upper surface 282 of the lens 208 may be smaller than, larger than, or of the same size with the surface of the bottom 280 of the lens 208 (as dictated by the needed optical properties of the lens 208).

The contact lens 208 may be manufactured from acrylic, glass, or other bio-compatible and optically viable materials used for the contact lens.

Referring to FIGS. 13 and 15A-15C, the ophthalmic contact gonioprism lens assembly 206 is anchored and stabilized, as well as centralized, at the desired site on the eye by the anchoring system 210 configured with the anchoring member 216 on the wire member 218 attached to the side wall 286 of lens holder 212, or, alternatively, to the side wall 284 of the gonioprism lens 208.

Alternatively, the wire member 218 may be attached by the end 220 thereof at another surface of the contact lens holder 212 (or the contact lens 208), such as, for example, the top surface 288 of the lens holder 212 or the upper surface 282 of the contact gonioprism lens 208.

As shown in FIG. 13, the annularly shaped contact lens holder 212 has an annularly shaped bottom 290 (with concentrically spaced apart inner and outer peripheral edges) and an annularly shaped upper surface 288 (with concentrically spaced apart inner and outer peripheral edges). The circumferential outside walls 292 extend between the outer peripheral edges of the bottom surface 290 and the outer peripheral edges of the upper surface 288.

Internal walls 294 extend between the inner peripheral edges of the annularly shaped bottom surface 290 and the upper surface 288, respectively, of the contact lens holder 212, and define a circularly shaped holder opening 296 therebetween.

The bottom surface 280 of the contact lens 208 and the circumferentially shaped holder opening 296 of the contact lens holder 212 are shaped and dimensioned to correspond each to the other to permit the bottom 280 of the lens 208 to pass through the circumferentially shaped holder opening 296.

Prior to the procedure, the contact lens holder 212 is positioned over the cornea 262, and the contact lens 208 is received in the holder opening 296 of the contact lens holder 212. The surgeon lowers the contact lens assembly 206 into contact with the tear film and viscous solution film 264 and brings the anchoring units 214, 216 in contact one with another (as shown in FIGS. 15B-15C).

During positioning of the contact lens holder assembly 206 on the eye 204, the surgeon can rotate the lens holder 212 relative to the wire member 218, as well as rotate the lens 208 inside the holder opening 296 in the contact lens holder 212, to adjust the position of the lens/lens holder relative to the patient's eye. When the anchoring units 214 and 216 are magnetically engaged one with another, stabilization and centralization of the contact lens assembly 206 in place is attained, and any deviation of the assembly 206 from the desired position during the ophthalmic procedure is prevented.

The lens holder 212 may be formed from polyether ether ketone (PEEK) material, or any other compound which is bio-compatible and capable of holding the contact lens 208 in position.

The height of the walls 286 of the lens holder 212 may be, for example, in the range of 1-2 mm, with the lens holder opening diameter ranging from 9 to 15 mm, for example, 11.5 mm.

As shown in FIG. 13, a partial cut-out 300 is formed in the lens holder 212 for surgical access/entry and visualization of the corneal incision. This cut-out 300 is positioned in relation to the site of the surgery so that the cut-out 300 is stabilized over the corneal or cataract incision. The configuration of the gonioprism contact lens assembly 206 shown in FIG. 13 permits the surgeon to view the incision site and to guide the surgical instrument into the anterior chamber of the eye for the ophthalmic surgery such as glaucoma surgery.

The ophthalmic procedure supported by the use of the subject non-sliding, non-sutured hands-free contact lens anchoring assembly is performed in the following sequence of operational steps:

The method begins in Step 1, wherein, as shown in FIG. 13, the subject corneal (macular) contact lens assembly 206 is formed which includes either the contact lens 208, or the contact lens 208 and the lens holder 212, and where the wire member 218 with the anchoring unit 216 is rotationally attached either to the lens 206 or the lens holder 212.

In Step 2, the modified eye speculum 230, shown in FIG. 14, is fabricated by securing the anchoring unit 214 (magnetically compatible with the anchoring unit 216 attached to the lens holder 212 via the wire member 218) to the wire loop member 248.

Subsequently, as shown in FIG. 15A, the subject method advances to Step 3 where the modified eye speculum 230 equipped with the anchoring unit 214 engages with the patient eye 204 to displace (widen) and stabilize the eyelids 260 as required by the ophthalmic procedure.

For being magnetically cooperative, the anchoring members 214, 216 are fabricated from magnetically attractable materials, such as magnetic materials/alloys, metal (or ferrous) materials/alloys, and their combination, meaning that at least one of the anchoring members (214 or 216) is made from a magnetic material, while another can be made from a magnetic material or a ferrous material to serve as a coupling member (plate). For example, when the anchoring member 216 secured to the contact lens holder 212 is fabricated from a magnetic alloy, the anchoring member 214 secured to the eye speculum 230 may be manufactured either as a magnet or as a ferrous coupling plate. Reciprocally, when the anchoring member 214 is formed from a magnetic alloy, the anchoring member 216 may be formed as a metallic (ferrous) coupling member.

In Step 4, subsequent to Step 3, the subject contact lens assembly 206 equipped with the subject anchoring system 210 is positioned in alignment the desired surgery site. During Step 4, shown in FIG. 15B, the surgeon may effectively adjust the lens holder orientation relative the wire member 218 by rotating the lens holder 212 relative to the wire member 218, as well as by rotation of the contact lens 208 within the opening 296 of the lens holder 212 (as shown in FIG. 13 by the arrows A and B). Additionally, the surgeon can displace the anchoring member 216 along the wire member 218 (as shown by the arrows C in FIG. 13), for the benefits of the preciseness and convenience of the lens/lens holder positioning at the desired location.

Once the desired position and orientation of the contact lens assembly 206 is found in Step 4, as shown in FIG. 15B-15C, the surgeon brings the anchoring members 214 and 216 in contact each with the other to magnetically connect one to another, thus anchoring and stabilizing the position/orientation of the contact lens assembly 206 on the eye 204, so that the surgeon can perform the ophthalmic procedure, such as the vitreoretinal surgery or macular surgery. During the procedure, the subject contact lens assembly 206 allows the surgeon to visualize the macular and other structures of the eye in high magnification. The contact lens assembly remains stabilized and centered on the cornea of the eye and is prevented from slipping from the desired surgical site.

The surgery is performed in a hands-free manner, when the surgeon (or the surgeon's assistant) does not have to manually locate and relocate the subject contact lens assembly. Non-sutured stabilization and centralization of the subject contact lens assembly and prevention from sliding from the desired surgical site is provided by the subject anchoring system supported by magnetic attraction between the anchoring members 214 and 216 secured, respectively, to the lens holder 212 and the eye speculum 230.

Upon completion of the surgery procedure, the surgeon disengages anchoring member 214 and 216, and removes the contact lens assembly 206 from the eye 204. The tissues of the eye are not traumatized in any way by the subject anchoring mechanism.

Subsequent to the surgery, the subject assembly 206 may be discarded (optionally) or sent for disinfection for use in other procedures.

The contact lens holder 212 may be secured to the contact lens 208 through an adhesive bonding or some other like technique. Contact lens holder 212 is fixed to the contact lens 208 at least partially along a periphery of the contact lens 208. In this manner, the contact lens holder 212 is fixedly attached to the contact lens 208. The function of the contact lens holder 212 is to provide support and stabilization of the contact lens 208 when the contact lens 208 is positioned over a medical procedure site of a patient's eye.

The contact lens holder 212 is fixedly secured to the contact lens 208 throughout or at least a portion of the periphery of the contact lens 208. The contact lens holder 212 may be formed of a polygonal or circular cross-sectional contour tubing for matingly interfacing with the contact lens 208. The contact lens holder 212 is formed by a substantially cylindrical tubing which receives the contact lens 208. However, the particular contour of the contact lens holder 212 is not important to the inventive concept as herein described with the exception that it is adhered to at least a portion of the contact lens 208 in order to securely hold the contact lens 208 within the contact lens holder 212. The contact lens holder 212 may be composed of a solid composition which is bio-compatible, such as stainless steel or some like composition which is substantially rigid.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is claimed is:

1. A contact lens system for ophthalmic procedures, comprising:
a contact lens assembly having a contact lens adapted for contacting an eye of a patient, and a contact lens holder secured to said contact lens;
an eye speculum configured with a threaded member extending in axial direction for radially displacing a pair of speculum arm members, each speculum arm member being equipped with a wire loop member secured at a distal end thereof, said wire loop member being applied to the eyelids of a patient during an ophthalmic procedure to displace and stabilize the eyelids; and,
a magnetically actuated anchoring mechanism operatively coupled between said eye speculum and said contact lens assembly, said anchoring mechanism including first and second magnetically cooperating anchoring members and a wire member secured, at one end thereof, to said contact lens holder, said first anchoring member being secured to at least one of said wire loop members of said eye speculum at a predetermined position thereat, and said second anchoring member being operatively coupled to said contact lens assembly and attached to said wire member in a displaceable relationship therewith along said wire member, whereby, during the ophthalmic procedure, said first and second anchoring members are disposed in a magnetic engagement one with another, resulting in an anchoring and stabilizing of said contact lens assembly at a desired position relative to the eye of the patient.

2. The contact lens system as recited in claim 1, where said anchoring mechanism is configured for retaining said contact lens at a selected procedure site during said ophthalmic procedure.

3. The contact lens system as recited in claim 1, further including a rotational mechanism operatively coupled between said wire member and said contact lens assembly, wherein said wire member defines a longitudinal axis along a length thereof, and said rotational mechanism supports rotational displacement of said contact lens assembly relative to the longitudinal axis of said wire member.

4. The contact lens system as recited in claim 1, wherein said contact lens is coupled to said contact lens holder in a co-axial rotationally displaceable relation therewith about the longitudinal axis of said contact lens holder.

5. The contact lens system as recited in claim 1, where said contact lens holder is fixedly secured to said contact lens at a periphery of said contact lens.

6. The contact lens system as recited in claim 5, where said contact lens holder is formed of a cylindrical tubing for receiving said contact lens.

7. The contact lens system as recited in claim 6, where said contact lens holder is adhered to said contact lens at at least a portion of said contact lens periphery.

8. The contact lens system as recited in claim 1, where said pair of wire loop members extending at said respective speculum arm members are displaced each from the other for maintaining said patient's eyelid in a stable displaced position, and wherein said first anchoring member is stably displaced at a predetermined position relative to said eyelid during the ophthalmic procedure.

9. The contact lens system as recited in claim 1, wherein each of said first and second anchoring members are fabricated from magnetically attractable materials selected from a group consisting of: a magnetic material, metal material, and a combination thereof.

10. The contact lens system as recited in claim 9, wherein one of said first and second anchoring members is fabricated from a metal alloy, and wherein another of said first and second anchoring members is fabricated from a ferrous material.

11. The contact lens system as recited in claim 1,
wherein said contact lens is configured with a bottom surface configured for contact with the eye, an upper surface, and side walls extending circumferentially between an edge of said bottom eye contact surface and an edge of said upper surface; and
wherein said contact lens holder is an annularly contoured contact lens holder configured with:
an annularly shaped bottom surface having inner and outer concentrically spaced apart edges;
an annularly shaped upper surface having inner and outer concentrically spaced apart edges,
outer walls extending circumferentially along and between said outer edges of said annularly shaped bottom and upper surfaces, respectively, of said annularly contoured contact lens holder, and
internal walls extending circumferentially along and between said inner edges of said annularly shaped bottom and upper surfaces, respectively, of said annularly contoured contact lens holder and defining a holder opening therebetween, said holder opening being shaped and dimensioned in correspondence to said bottom surface of said contact lens.

12. The contact lens system as recited in claim 11, wherein said contact lens is received in said holder opening of said annularly contoured contact lens holder and maintained with said bottom surface in contact with the tissues of the eye at the desired procedure site by said annularly contoured contact lens holder anchored at said desired procedure site by said magnetically actuated anchoring mechanism.

13. The contact lens system as recited in claim 11, wherein said outer walls of said annularly contoured contact lens holder are shaped with a cut-out portion extending a predetermined length along said outer walls for surgical tools access and visualization of said desired procedure site.

14. The contact lens system as recited in claim 11, wherein said annularly contoured contact lens holder is fabricated from a material selected from the group of: surgical steel, bio-compatible plastic, polyether ether ketone (PEEK), polymer, and combination thereof.

15. The contact lens system as recited in claim 1, wherein said contact lens is selected from the group of a corneal lens and a gonioprism contact lens.

16. A method of performing an ophthalmic procedure, comprising:
configuring a contact lens assembly comprising:
a contact lens adapted for contacting an eye of a patient, and a contact lens holder secured to said contact lens;
configuring an eye speculum with a threaded member extending in axial direction for radially displacing a pair of speculum arm members, each terminating in a wire loop member at a distal end thereof,
securing a first magnetically cooperative anchoring member at a predetermined position on at least one of said wire loop members;
configuring a magnetically actuated anchoring mechanism operatively coupling said contact lens assembly and said respective wire loop member of the eye speculum, said anchoring mechanism including said first magnetically cooperative anchoring member, a wire member secured, at one end thereof, to said contact lens holder, and a second magnetically cooperative anchoring member operatively coupled to said contact lens assembly and attached to said wire member in a displaceable relationship therewith along said wire member;
placing said contact lens assembly over a desired procedure site;
applying said eye speculum to the eyelids to displace and stabilize the eyelids, thus securing said first magnetically cooperative anchoring member at a predetermined position at the eyelid;
bringing said first and second magnetically cooperative anchoring members in contact one with another to thereby magnetically engage one with another and anchor said contact lens assembly at a desired position relative to the eye of the patient;
performing said ophthalmic procedure;
upon completion of said ophthalmic procedure, disengaging said first and second magnetically cooperative anchoring members, thus de-actuating said anchoring mechanism;
removing said contact lens assembly from the operational side; and
removing said eye speculum from the patient's eye.

* * * * *